(12) United States Patent
Seavey et al.

(10) Patent No.: US 11,672,576 B2
(45) Date of Patent: *Jun. 13, 2023

(54) ORTHOPEDIC IMPLANT AND METHODS OF IMPLANTING AND REMOVING SAME

(71) Applicant: Howmedica Osteonics Corp., Mahwah, NJ (US)

(72) Inventors: Jeff F. Seavey, Houston, TX (US); Lance N. Terrill, Glounthaune (IE); Kasey A. Kilgore, Houston, TX (US)

(73) Assignee: Howmedica Osteonics Corp., Mahwah, NJ (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/891,732

(22) Filed: Jun. 3, 2020

(65) Prior Publication Data

US 2020/0289176 A1 Sep. 17, 2020

Related U.S. Application Data

(62) Division of application No. 15/669,370, filed on Aug. 4, 2017, now Pat. No. 10,702,318, which is a division
(Continued)

(51) Int. Cl.
*A61B 17/72* (2006.01)
*A61F 2/42* (2006.01)
(Continued)

(52) U.S. Cl.
CPC ...... *A61B 17/7291* (2013.01); *A61B 17/1617* (2013.01); *A61B 17/1682* (2013.01);
(Continued)

(58) Field of Classification Search
CPC ............ A61B 17/7291; A61B 17/1617; A61B 17/1682; A61B 17/68; A61B 17/863; A61B 17/8872; A61F 2/4225
See application file for complete search history.

(56) References Cited

U.S. PATENT DOCUMENTS 1,095,054 A 4/1914 Wiesenfeld
1,517,334 A 12/1924 Young
(Continued)

FOREIGN PATENT DOCUMENTS

CA 2836654 A1 6/2014
CA 2837497 A1 6/2014
(Continued)

OTHER PUBLICATIONS

EP Notification for Application No. 09741356.1 dated Feb. 12, 2015, 4 pages.
HammerFix IP Fusion System, Hammertoe Deformity Surgical Technique, designed by Extremity Medical, published Mar. 31, 2014 (8 pages).
International Search Report for PCT/FR2008/050453 dated Nov. 4, 2008, 4 pages.
(Continued)

*Primary Examiner* — Suba Ganesan
(74) *Attorney, Agent, or Firm* — Lerner David LLP

(57) ABSTRACT

Illustrative embodiments of orthopedic implants and methods for surgically repairing hammertoe are disclosed. According to at least one illustrative embodiment, an orthopedic implant includes a proximal segment comprising a number of spring arms forming an anchored barb at a first end of the implant, a distal segment extending between the proximal segment and a second end of the implant, and a central segment disposed between the proximal and distal segment.

20 Claims, 11 Drawing Sheets

Related U.S. Application Data of application No. 14/637,032, filed on Mar. 3, 2015, now Pat. No. 9,757,168.

(51) Int. Cl.
| | |
|---|---|
| *A61B 17/86* | (2006.01) |
| *A61B 17/88* | (2006.01) |
| *A61B 17/16* | (2006.01) |
| *A61B 17/68* | (2006.01) |

(52) U.S. Cl.
CPC ............ *A61B 17/68* (2013.01); *A61B 17/863* (2013.01); *A61B 17/888* (2013.01); *A61B 17/8872* (2013.01); *A61B 17/8883* (2013.01); *A61F 2/4225* (2013.01); *A61B 17/7266* (2013.01); *A61F 2002/4228* (2013.01)

(56) References Cited

U.S. PATENT DOCUMENTS

| | | | |
|---|---|---|---|
| 1,893,864 A | 1/1933 | Kocher | |
| 2,128,005 A | 8/1938 | Lombard | |
| 2,208,848 A | 7/1940 | Jorgensen | |
| 2,531,911 A | 11/1950 | Johnson | |
| 2,580,821 A | 1/1952 | Nicola | |
| 2,984,248 A | 5/1961 | Sidelman | |
| 3,338,689 A | 8/1967 | Hetzel et al. | |
| 3,462,765 A | 8/1969 | Swanson | |
| 3,466,669 A | 9/1969 | Flatt | |
| 3,593,342 A | 7/1971 | Niebauer et al. | |
| 3,681,786 A | 8/1972 | Lynch | |
| 3,739,403 A | 6/1973 | Nicolle | |
| 3,805,302 A | 4/1974 | Mathys | |
| 3,824,631 A | 7/1974 | Burstein et al. | |
| 3,875,594 A | 4/1975 | Swanson | |
| D243,716 S | 3/1977 | Treace et al. | |
| 4,091,806 A | 5/1978 | Aginsky et al. | |
| 4,158,893 A | 6/1979 | Swanson | |
| 4,204,284 A | 5/1980 | Koeneman | |
| 4,237,875 A | 12/1980 | Termanini | |
| 4,276,660 A | 7/1981 | Laure | |
| 4,364,382 A | 12/1982 | Mennen | |
| 4,367,562 A | 1/1983 | Gauthier et al. | |
| 4,485,816 A | 12/1984 | Krumme | |
| D277,509 S | 2/1985 | Lawrence et al. | |
| D277,784 S | 2/1985 | Sgarlato et al. | |
| 4,522,200 A | 6/1985 | Stednitz | |
| D284,099 S | 6/1986 | Laporta et al. | |
| 4,634,382 A | 1/1987 | Kusano et al. | |
| D291,731 S | 9/1987 | Aikins | |
| 4,759,768 A | 7/1988 | Hermann et al. | |
| 4,871,367 A | 10/1989 | Christensen et al. | |
| 4,905,679 A | 3/1990 | Morgan | |
| 4,955,916 A | 9/1990 | Carignan et al. | |
| 4,969,909 A | 11/1990 | Barouk | |
| 5,011,497 A | 4/1991 | Persson et al. | |
| 5,047,059 A | 9/1991 | Saffar | |
| 5,062,851 A | 11/1991 | Branemark | |
| 5,074,865 A | 12/1991 | Fahmy | |
| 5,092,896 A | 3/1992 | Meuli et al. | |
| 5,108,443 A | 4/1992 | Branemark | |
| 5,133,761 A | 7/1992 | Krouskop | |
| 5,179,915 A | 1/1993 | Cohen et al. | |
| 5,190,546 A | 3/1993 | Jervis | |
| 5,207,712 A | 5/1993 | Cohen | |
| 5,326,364 A | 7/1994 | Clift, Jr. et al. | |
| 5,360,450 A | 11/1994 | Giannini | |
| 5,382,251 A | 1/1995 | Hood et al. | |
| 5,405,400 A | 4/1995 | Linscheid et al. | |
| 5,405,401 A | 4/1995 | Lippincott, III et al. | |
| 5,425,776 A | 6/1995 | Cohen | |
| 5,425,777 A | 6/1995 | Sarkisian et al. | |
| 5,454,814 A | 10/1995 | Comte | |
| 5,464,427 A | 11/1995 | Curtis et al. | |
| 5,474,557 A | 12/1995 | Mai | |
| D366,114 S | 1/1996 | Ohata | |
| 5,480,447 A | 1/1996 | Skiba | |
| 5,484,443 A | 1/1996 | Pascarella et al. | |
| D369,412 S | 4/1996 | Morgan | |
| 5,507,822 A | 4/1996 | Bouchon et al. | |
| 5,522,903 A | 6/1996 | Sokolow et al. | |
| 5,554,157 A | 9/1996 | Errico et al. | |
| 5,578,036 A | 11/1996 | Stone et al. | |
| 5,634,925 A | 6/1997 | Urbanski | |
| 5,674,297 A | 10/1997 | Lane et al. | |
| 5,690,631 A | 11/1997 | Duncan et al. | |
| 5,702,472 A | 12/1997 | Huebner | |
| D388,877 S | 1/1998 | Morgan | |
| 5,725,585 A | 3/1998 | Zobel | |
| 5,779,707 A | 7/1998 | Bertholet et al. | |
| 5,782,927 A | 7/1998 | Klawitter et al. | |
| 5,824,095 A | 10/1998 | Di Maio, Jr. et al. | |
| 5,876,434 A | 3/1999 | Flomenblit et al. | |
| 5,882,444 A | 3/1999 | Flomenblit et al. | |
| 5,919,193 A | 7/1999 | Slavitt | |
| 5,951,288 A | 9/1999 | Sawa | |
| 5,958,159 A | 9/1999 | Prandi | |
| 5,984,970 A | 11/1999 | Bramlet | |
| 5,984,971 A | 11/1999 | Faccioli et al. | |
| 6,011,497 A | 1/2000 | Tsang et al. | |
| 6,017,366 A | 1/2000 | Berman | |
| 6,093,188 A | 7/2000 | Murray | |
| 6,123,709 A | 9/2000 | Jones | |
| 6,146,387 A | 11/2000 | Trott et al. | |
| 6,162,234 A | 12/2000 | Freedland et al. | |
| 6,197,037 B1 | 3/2001 | Hair | |
| 6,200,330 B1 | 3/2001 | Benderev et al. | |
| 6,248,109 B1 | 6/2001 | Stoffella | |
| 6,261,289 B1 | 7/2001 | Levy | |
| 6,319,284 B1 | 11/2001 | Rushdy et al. | |
| 6,325,805 B1 | 12/2001 | Ogilvie et al. | |
| 6,348,052 B1 | 2/2002 | Sammarco | |
| 6,352,560 B1 | 3/2002 | Poeschmann et al. | |
| 6,383,223 B1 | 5/2002 | Baehler et al. | |
| 6,386,877 B1 | 5/2002 | Sutter | |
| 6,395,031 B1 | 5/2002 | Foley et al. | |
| 6,413,260 B1 | 7/2002 | Berrevoets et al. | |
| 6,423,097 B2 | 7/2002 | Rauscher | |
| 6,428,634 B1 | 8/2002 | Besselink et al. | |
| 6,454,808 B1 | 9/2002 | Masada | |
| 6,458,134 B1 | 10/2002 | Songer et al. | |
| 6,475,242 B1 | 11/2002 | Bramlet | |
| 6,517,543 B1 | 2/2003 | Berrevoets et al. | |
| 6,554,833 B2 | 4/2003 | Levy et al. | |
| 6,689,169 B2 | 2/2004 | Harris | |
| 6,692,499 B2 | 2/2004 | Tormala et al. | |
| 6,699,247 B2 | 3/2004 | Zucherman et al. | |
| 6,699,292 B2 | 3/2004 | Ogilvie et al. | |
| 6,706,045 B2 | 3/2004 | Lin et al. | |
| 6,736,818 B2 | 5/2004 | Perren et al. | |
| 6,773,437 B2 | 8/2004 | Ogilvie et al. | |
| 6,811,568 B2 | 11/2004 | Minamikawa | |
| 6,827,741 B2 | 12/2004 | Reeder | |
| 6,869,449 B2 | 3/2005 | Ball et al. | |
| 6,896,177 B2 | 5/2005 | Carter | |
| 6,981,974 B2 | 1/2006 | Berger | |
| 7,025,789 B2 | 4/2006 | Chow et al. | |
| 7,037,342 B2 | 5/2006 | Nilsson et al. | |
| 7,041,106 B1 | 5/2006 | Carver et al. | |
| 7,044,953 B2 | 5/2006 | Capanni | |
| 7,182,787 B2 | 2/2007 | Hassler et al. | |
| 7,240,677 B2 | 7/2007 | Fox | |
| 7,291,175 B1 | 11/2007 | Gordon | |
| 7,588,603 B2 | 9/2009 | Leonard | |
| 7,600,956 B2 | 10/2009 | McDuff et al. | |
| 7,780,737 B2 | 8/2010 | Bonnard et al. | |
| 7,794,483 B2 | 9/2010 | Capanni | |
| 7,837,738 B2 | 11/2010 | Reigstad et al. | |
| 7,842,091 B2 | 11/2010 | Johnstone et al. | |
| 7,909,880 B1 | 3/2011 | Grant | |
| 7,922,765 B2 | 4/2011 | Reiley | |
| 7,955,388 B2 | 6/2011 | Jensen et al. | |
| 7,976,580 B2 | 7/2011 | Berger | |
| 8,100,983 B2 | 1/2012 | Schulte | |

(56) References Cited

U.S. PATENT DOCUMENTS

| | | |
|---|---|---|
| 8,162,942 B2 | 4/2012 | Coati et al. |
| 8,262,712 B2 | 9/2012 | Coilard-Lavirotte et al. |
| 8,394,097 B2 | 3/2013 | Peyrot et al. |
| 8,414,583 B2 | 4/2013 | Prandi et al. |
| 8,475,456 B2 | 7/2013 | Augoyard et al. |
| 8,529,611 B2 | 9/2013 | Champagne et al. |
| 8,597,337 B2 | 12/2013 | Champagne |
| 8,608,785 B2 | 12/2013 | Reed et al. |
| 8,685,024 B2 | 4/2014 | Roman |
| 8,715,325 B2 | 5/2014 | Weiner et al. |
| 8,734,491 B2 | 5/2014 | Seavey |
| 8,834,483 B2 | 9/2014 | Cheney et al. |
| 8,834,572 B2 | 9/2014 | Averous et al. |
| 8,864,804 B2 | 10/2014 | Champagne et al. |
| 8,986,348 B2 | 3/2015 | Reiley |
| 8,998,999 B2 | 4/2015 | Lewis et al. |
| 9,011,504 B2 | 4/2015 | Reed |
| 9,044,287 B2 | 6/2015 | Reed et al. |
| 9,056,014 B2 | 6/2015 | McCormick et al. |
| 9,072,562 B2 | 7/2015 | Weiner et al. |
| 9,072,564 B2 | 7/2015 | Reed et al. |
| 9,125,698 B2 | 9/2015 | Miller |
| 9,125,704 B2 | 9/2015 | Reed et al. |
| 9,282,977 B2 | 3/2016 | Penzimer et al. |
| 9,452,002 B2 | 9/2016 | Roman et al. |
| 9,498,266 B2 | 11/2016 | McCormick et al. |
| 9,498,273 B2 | 11/2016 | Thoren et al. |
| 9,554,914 B2 | 1/2017 | Taylor et al. |
| 9,724,140 B2 | 8/2017 | McCormick |
| 9,757,168 B2 | 9/2017 | Seavey et al. |
| 9,775,630 B2 | 10/2017 | Leavitt et al. |
| 10,022,167 B2 | 7/2018 | Augoyard et al. |
| 10,111,690 B2 | 10/2018 | Anderson et al. |
| 2001/0025199 A1 | 9/2001 | Rauscher |
| 2001/0049529 A1 | 12/2001 | Cachia et al. |
| 2002/0019636 A1 | 2/2002 | Ogilvie et al. |
| 2002/0055785 A1 | 5/2002 | Harris |
| 2002/0065561 A1 | 5/2002 | Ogilvie et al. |
| 2002/0068939 A1 | 6/2002 | Levy et al. |
| 2002/0082705 A1 | 6/2002 | Bouman et al. |
| 2002/0099395 A1 | 7/2002 | Acampora et al. |
| 2002/0133156 A1 | 9/2002 | Cole |
| 2002/0189622 A1 | 12/2002 | Cauthen et al. |
| 2003/0040805 A1 | 2/2003 | Minamikawa |
| 2003/0069645 A1 | 4/2003 | Ball et al. |
| 2003/0120277 A1 | 6/2003 | Berger |
| 2003/0130660 A1 | 7/2003 | Levy et al. |
| 2004/0002759 A1 | 1/2004 | Ferree |
| 2004/0093081 A1 | 5/2004 | Nilsson et al. |
| 2004/0102853 A1 | 5/2004 | Boumann et al. |
| 2004/0138756 A1 | 7/2004 | Reeder |
| 2004/0220678 A1 | 11/2004 | Chow et al. |
| 2004/0230193 A1 | 11/2004 | Cheung et al. |
| 2005/0065589 A1 | 3/2005 | Schneider et al. |
| 2005/0119757 A1 | 6/2005 | Hassler et al. |
| 2005/0124990 A1 | 6/2005 | Teague et al. |
| 2005/0216015 A1* | 9/2005 | Kreidler ............... B25B 23/106 606/104 |
| 2005/0251265 A1 | 11/2005 | Ruccio et al. |
| 2005/0261768 A1 | 11/2005 | Trieu |
| 2005/0283159 A1 | 12/2005 | Amara |
| 2006/0015181 A1 | 1/2006 | Elberg |
| 2006/0052725 A1 | 3/2006 | Santilli |
| 2006/0052878 A1 | 3/2006 | Schmieding |
| 2006/0074492 A1 | 4/2006 | Frey |
| 2006/0084998 A1 | 4/2006 | Levy et al. |
| 2006/0085075 A1 | 4/2006 | McLeer |
| 2006/0247787 A1 | 11/2006 | Rydell et al. |
| 2007/0038303 A1 | 2/2007 | Myerson et al. |
| 2007/0123993 A1 | 5/2007 | Hassler et al. |
| 2007/0142920 A1 | 6/2007 | Niemi |
| 2007/0156241 A1 | 7/2007 | Reiley et al. |
| 2007/0162018 A1 | 7/2007 | Jensen et al. |
| 2007/0185584 A1 | 8/2007 | Kaufmann et al. |
| 2007/0198088 A1 | 8/2007 | Biedermann et al. |
| 2007/0213831 A1 | 9/2007 | de Cubber |
| 2007/0233110 A1* | 10/2007 | Muhanna ............ A61B 17/8615 606/86 A |
| 2007/0239158 A1 | 10/2007 | Trieu et al. |
| 2008/0039949 A1 | 2/2008 | Meesenburg et al. |
| 2008/0132894 A1 | 6/2008 | Coilard-Lavirotte et al. |
| 2008/0154385 A1 | 6/2008 | Trail et al. |
| 2008/0177262 A1 | 7/2008 | Augoyard et al. |
| 2008/0195219 A1 | 8/2008 | Wiley et al. |
| 2008/0221697 A1 | 9/2008 | Graser |
| 2008/0221698 A1 | 9/2008 | Berger |
| 2008/0234763 A1 | 9/2008 | Patterson et al. |
| 2008/0269908 A1 | 10/2008 | Warburton |
| 2009/0005821 A1 | 1/2009 | Chirico et al. |
| 2009/0012564 A1 | 1/2009 | Chirico et al. |
| 2009/0254189 A1 | 10/2009 | Scheker |
| 2009/0254190 A1 | 10/2009 | Gannoe et al. |
| 2010/0010637 A1 | 1/2010 | Pequignot |
| 2010/0016905 A1 | 1/2010 | Greenhalgh et al. |
| 2010/0016982 A1 | 1/2010 | Solomons |
| 2010/0057214 A1 | 3/2010 | Graham et al. |
| 2010/0121390 A1 | 5/2010 | Kleinman |
| 2010/0131014 A1 | 5/2010 | Peyrot |
| 2010/0131072 A1 | 5/2010 | Schulte |
| 2010/0161068 A1 | 6/2010 | Lindner et al. |
| 2010/0185295 A1 | 7/2010 | Emmanuel |
| 2010/0228301 A1 | 9/2010 | Greenhalgh et al. |
| 2010/0249942 A1 | 9/2010 | Goswami et al. |
| 2010/0256770 A1 | 10/2010 | Hakansson et al. |
| 2010/0262254 A1 | 10/2010 | Lawrence et al. |
| 2011/0004317 A1 | 1/2011 | Hacking et al. |
| 2011/0144644 A1 | 6/2011 | Prandi et al. |
| 2011/0301652 A1 | 12/2011 | Reed et al. |
| 2011/0301653 A1 | 12/2011 | Reed et al. |
| 2012/0029579 A1 | 2/2012 | Bottlang et al. |
| 2012/0065692 A1 | 3/2012 | Champagne et al. |
| 2012/0083791 A1 | 4/2012 | Cheney et al. |
| 2012/0089197 A1 | 4/2012 | Anderson |
| 2012/0259419 A1 | 10/2012 | Brown et al. |
| 2013/0053975 A1 | 2/2013 | Reed et al. |
| 2013/0060295 A1 | 3/2013 | Reed et al. |
| 2013/0066435 A1 | 3/2013 | Averous et al. |
| 2013/0123862 A1 | 5/2013 | Anderson et al. |
| 2013/0131822 A1 | 5/2013 | Lewis et al. |
| 2013/0150965 A1 | 6/2013 | Taylor et al. |
| 2013/0317559 A1 | 11/2013 | Leavitt et al. |
| 2014/0058462 A1 | 2/2014 | Reed et al. |
| 2014/0107712 A1 | 4/2014 | Fallin et al. |
| 2014/0142715 A1 | 5/2014 | McCormick |
| 2014/0180428 A1 | 6/2014 | McCormick |
| 2014/0188239 A1 | 7/2014 | Cummings |
| 2014/0309747 A1 | 10/2014 | Taylor et al. |
| 2015/0011998 A1 | 1/2015 | McCormick et al. |
| 2015/0066097 A1 | 3/2015 | Biedermann |
| 2015/0073413 A1 | 3/2015 | Palmer et al. |
| 2015/0094778 A1 | 4/2015 | McCormick et al. |
| 2015/0112341 A1 | 4/2015 | Penzimer et al. |
| 2015/0112446 A1 | 4/2015 | Melamed et al. |
| 2015/0223848 A1 | 8/2015 | McCormick |
| 2015/0223849 A1 | 8/2015 | McCormick et al. |
| 2015/0223853 A1 | 8/2015 | Appenzeller et al. |
| 2017/0239059 A1 | 8/2017 | Boublil et al. |
| 2017/0252084 A1 | 9/2017 | Anderson et al. |
| 2017/0333081 A1 | 11/2017 | Cordier et al. |
| 2018/0021145 A1 | 1/2018 | Seavey et al. |

FOREIGN PATENT DOCUMENTS

| | | |
|---|---|---|
| EP | 0420794 A1 | 4/1991 |
| EP | 1300122 A2 | 4/2003 |
| EP | 1923012 A1 | 5/2008 |
| FR | 2725126 A1 | 4/1996 |
| FR | 2783702 A1 | 3/2000 |
| FR | 2787313 A1 | 6/2000 |
| FR | 2794019 A1 | 12/2000 |
| FR | 2801189 A1 | 5/2001 |
| FR | 2846545 A1 | 5/2004 |
| FR | 2884406 | 10/2006 |
| GB | 2119655 A | 11/1983 |

(56) References Cited

FOREIGN PATENT DOCUMENTS

| | | | |
|---|---|---|---|
| GB | 2430625 | B | 4/2007 |
| JP | S60145133 | A | 7/1985 |
| JP | 03001854 | A | 8/1991 |
| JP | H7303662 | A | 11/1995 |
| JP | 2004535249 | A | 11/2004 |
| JP | 2007530194 | A | 11/2007 |
| JP | 2008188411 | A | 8/2008 |
| JP | 2008537696 | A | 9/2008 |
| WO | 9641596 | A1 | 12/1996 |
| WO | 9733537 | A1 | 9/1997 |
| WO | 2005063149 | A1 | 7/2005 |
| WO | 2005104961 | A1 | 11/2005 |
| WO | 2006109004 | A1 | 10/2006 |
| WO | 2008057404 | A2 | 5/2008 |
| WO | 2008112308 | A1 | 9/2008 |
| WO | 2008129214 | A2 | 10/2008 |
| WO | 2009103085 | A1 | 8/2009 |
| WO | 2011130229 | A1 | 10/2011 |
| WO | 2015136212 | A1 | 9/2015 |

OTHER PUBLICATIONS

International Search Report, PCT/FR2006/050345, dated Aug. 30, 2006, 3 pages.
Intraosseous Fixation System, Hammertoe Surgical Technique, designed by OrthoHelix, published Aug. 23, 2012 (16 pages).
Japanese Office Action for Application No. 2011-526540 dated Aug. 13, 2013, 3 pages.
Patent Owner's Preliminary Response and Exhibits List, IPR2022-00486 of U.S. Pat. No. 9,168,074 , *OsteoMed LLC* v. *Stryker European Operations Holdings LLC*. (Filed May 16, 2022), 77 pages. [Including Appendices at Exhibits 2003 and 2004].
Collins English Dictionary Excerpt (Jun. 2007), 6 pages. [Exhibit No. 2001 to Patent Owner's Preliminary Response, IPR2022-00486 of U.S. Pat. No. 9,168,074 filed May 16, 2022].
Excerpt from Tool.com—File and Rasp Tools, (Copyright 2022), 6 pages. [Exhibit No. 2002 to Patent Owner's Preliminary Response, IPR2022-00486 of U.S. Pat. No. 9,168,074 filed May 16, 2022].
Jung, H. J. et al., JJ., Decision Denying Institution of Inter Partes Review, IPR2022-00486 of U.S. Pat. No. 9,168,074 , *OsteoMed LLC* v. *Stryker European Operations Holdings LLC*. (Aug. 12, 2022). 42 pages.

\* cited by examiner

ORTHOPEDIC IMPLANT AND METHODS OF IMPLANTING AND REMOVING SAME

CROSS-REFERENCE TO RELATED APPLICATION

The present application is a divisional of U.S. patent application Ser. No. 15/669,370, filed on Aug. 4, 2017, which is a divisional of U.S. patent application Ser. No. 14/637,032 (now U.S. Pat. No. 9,757,168) filed Mar. 3, 2015, the disclosures of which are incorporated herein by reference.

TECHNICAL FIELD

The present disclosure relates generally to orthopedic implants. More particularly, the present disclosure relates to orthopedic implants for surgically repairing joints and methods of implanting and removing same.

BACKGROUND OF THE INVENTION

A hammertoe is condition in which the proximal interphalangeal joints of the second, third, fourth, or fifth toe has become deformed, thereby causing the toe to be permanently bent. Hammertoe occurs from a muscle and ligament imbalance around the joints between the toes, which causes the joints to bend and become stuck in a bent position. Hammertoe oftentimes causes painful rubbing and irritation on the top of the bent toe. If caring for any callouses or corns, changing ones footwear, and/or utilizing cushions, supports, or comfort devices in ones shoes do not alleviate the pain associate with hammertoe, surgical intervention may be required to alleviate the pain. A procedure may be utilized to anatomically correct the joint using a pin, screw, or other implant. After anatomical correction, fusion or bony consolidation of the joint area occurs.

SUMMARY OF THE INVENTION

The present application discloses one or more of the features recited in the appended claims and/or the following features which alone or in any combination, may comprise patentable subject matter.

According to a first aspect of the present disclosure, an orthopedic implant may include a proximal segment comprising at least three spring arms forming an anchored barb at a first end of the implant, wherein first threading extends around outer surfaces of at least a portion of each spring arm and the first threading includes minor and major diameters. The surgical implant may further include a distal segment extending between the proximal segment and a second end of the implant and including second threading extending along at least a portion of the distal segment.

In some embodiments, at least two of the major diameters of the first threading may increase between the distal segment and the first end of the implant.

In some embodiments, each of the major diameters of the first threading may increase between the distal segment and the first end of the implant.

In some embodiments, the proximal segment may be configured to be implanted within a proximal phalanx of a patient and the distal segment may be configured to be threaded into a middle phalanx of the patient.

In some embodiments, the surgical implant may include a marking disposed on the surgical implant between the proximal and distal segments, wherein the marking may be configured to identify an optimal depth for implantation of the distal segment of the implant into a middle phalanx of a patient.

In some embodiments, the implant may be manufactured of polyetheretherketone (PEEK).

In some embodiments, the second threading may include minor diameters and major diameters and at least two of the minor diameters may increase between the second end and the proximal segment.

In some embodiments, each of the minor diameters of the second threading may increase between the second end and the proximal segment.

In some embodiments, the proximal segment may include a drive feature formed in an end thereof that is configured to accept a tool for removal of the implant from a phalanx.

According to a second aspect of the present disclosure, an orthopedic implant may include a proximal segment comprising at least two spring arms forming an anchored barb at a first end of the implant, wherein first threading may extend around outer surfaces of at least a portion of each spring arm and the first threading may include minor and major diameters. The surgical implant may further include a distal segment extending between the proximal segment and a second end of the implant and include second threading extending along at least a portion of the distal segment, wherein the second threading may include minor and major diameters and at least two of the minor diameters may increase between the second end and the proximal segment.

In some embodiments, each of the minor diameters of the second threading of the distal segment may increase between the second end and the proximal segment.

In some embodiments, each of the major diameters of the first threading of the proximal segment may increase between the distal segment and the first end of the implant.

In some embodiments, the proximal segment may be configured to be implanted within a proximal phalanx of a patient and the distal segment may be configured to be threaded into a middle phalanx of the patient.

In some embodiments, a marking may be disposed on the surgical implant between the proximal and distal segments, wherein the marking may be configured to identify an optimal depth for implantation of the distal segment of the implant into a middle phalanx of a patient.

In some embodiments, the implant may be manufactured of polyetheretherketone (PEEK).

In some embodiments, the proximal segment may include at least three spring arms forming the anchored barb at the first end of the implant.

In some embodiments, the proximal segment may include a drive feature formed in an end thereof that is configured to accept a tool for removal of the implant from a phalanx.

According to a third aspect of the present disclosure, a method of removing an orthopedic implant from a patient may include the step of severing an orthopedic implant in a central segment of the orthopedic implant that is disposed between a proximal segment configured for implantation within a proximal phalanx of the patient and a distal segment opposite the proximal segment and configured for implantation within a middle phalanx of the patient. The method may further include the steps of inserting a tool into the proximal or distal segment of the orthopedic implant and rotating the tool to remove the proximal or distal segment from the proximal or middle phalanx, respectively.

In some embodiments, the method may include one or more of the steps of severing the implant, inserting the tool, which is made of a high-strength stainless steel, into the distal segment, which is made of a polymeric material, to thereby tap the tool into the distal segment, and removing the distal segment from the middle phalanx.

In some embodiments, the method may include one or more of the steps of inserting the tool into an end of the proximal segment, mating a portion of the tool with a drive feature in the proximal segment of the implant, and rotating the tool to remove at least a portion of the surgical implant.

In some embodiments, the drive feature may include a plurality of semi-cylindrical channels.

According to a fourth aspect, a tool for implantation of an orthopedic implant having a proximal segment with at least three arms spaced from one another by recesses, the three arms configured for implantation with a proximal phalanx of a patient and a distal segment opposite the proximal segment and configured for implantation within a middle phalanx of the patient is disclosed. The implantation tool may include a body and at least three arms extending from an end of the body, wherein each of the arms is sized and shaped to fit within one of the recesses disposed between the three arms in the proximal segment of the implant.

In some embodiments, the arms may have an outer diameter that is less than an outer diameter of the arms of the proximal segment of the implant.

In some embodiments, the tool may be configured to retain the proximal segment of the implant on the end of the body.

BRIEF DESCRIPTION OF THE DRAWINGS

The concepts described in the present disclosure are illustrated by way of example and not by way of limitation in the accompanying figures. For simplicity and clarity of illustration, elements illustrated in the figures are not necessarily drawn to scale. For example, the dimensions of some elements may be exaggerated relative to other elements for clarity. Further, where considered appropriate, the same or similar reference labels have been repeated among the figures to indicate corresponding or analogous elements.

DETAILED DESCRIPTION

Figure 1:
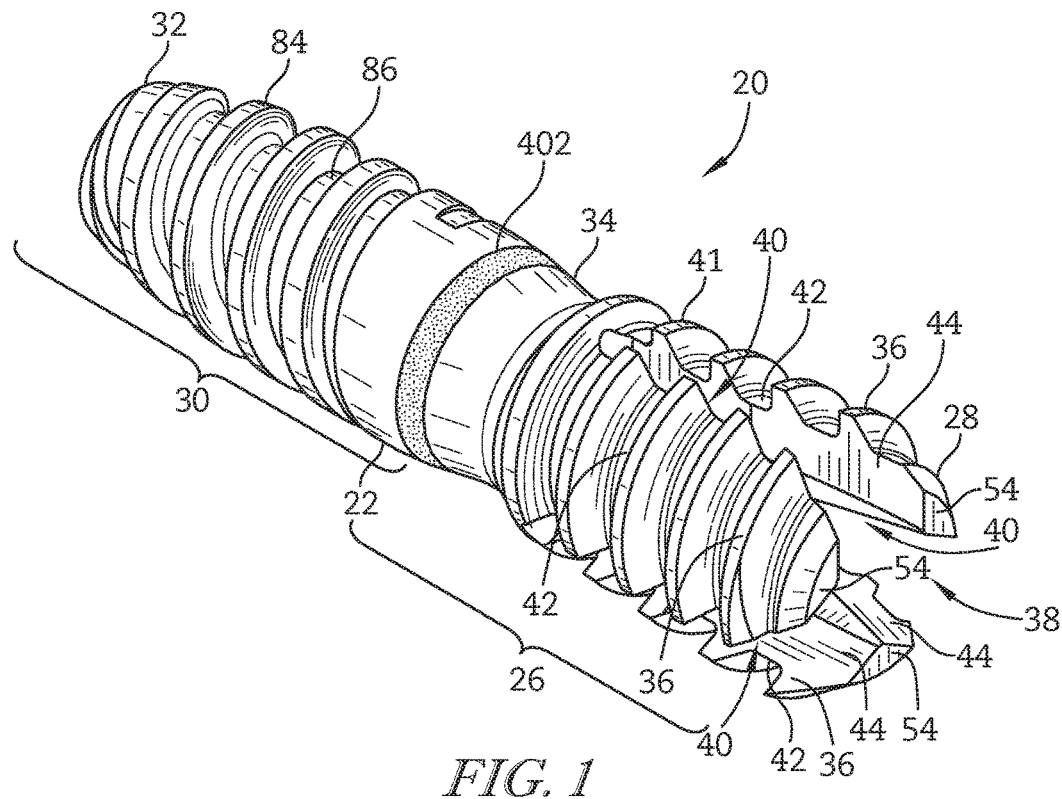
FIG. 1 is an isometric view of a first embodiment of an orthopedic implant taken generally from a first end of the implant.

While the concepts of the present disclosure are susceptible to various modifications and alternative forms, specific exemplary embodiments thereof have been shown by way of example in the figures and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the present disclosure.

A first embodiment of an orthopedic implant 20 suitable for treatment and correction of hammertoe is depicted in FIGS. 1-5. The implant 20 generally includes a pin-shaped body 22 extending along a longitudinal axis 24 and further includes a proximal segment 26 terminating in a first end 28 and a distal segment 30 terminating in a second end 32. The proximal and distal segments 26, 30 may be integral with one another and joined at a central, narrowed segment 34 of the implant 20. The proximal segment 26 of the body 22 may generally comprise the central, narrowed segment 34 and three spring arms 36 that form a barbed anchor 38 and which extend away from the central, narrowed segment 34. While the segment 34 is depicted as being narrowed, the segment 34 may alternatively not be narrowed or may have a constant outer diameter.

Figure 2:
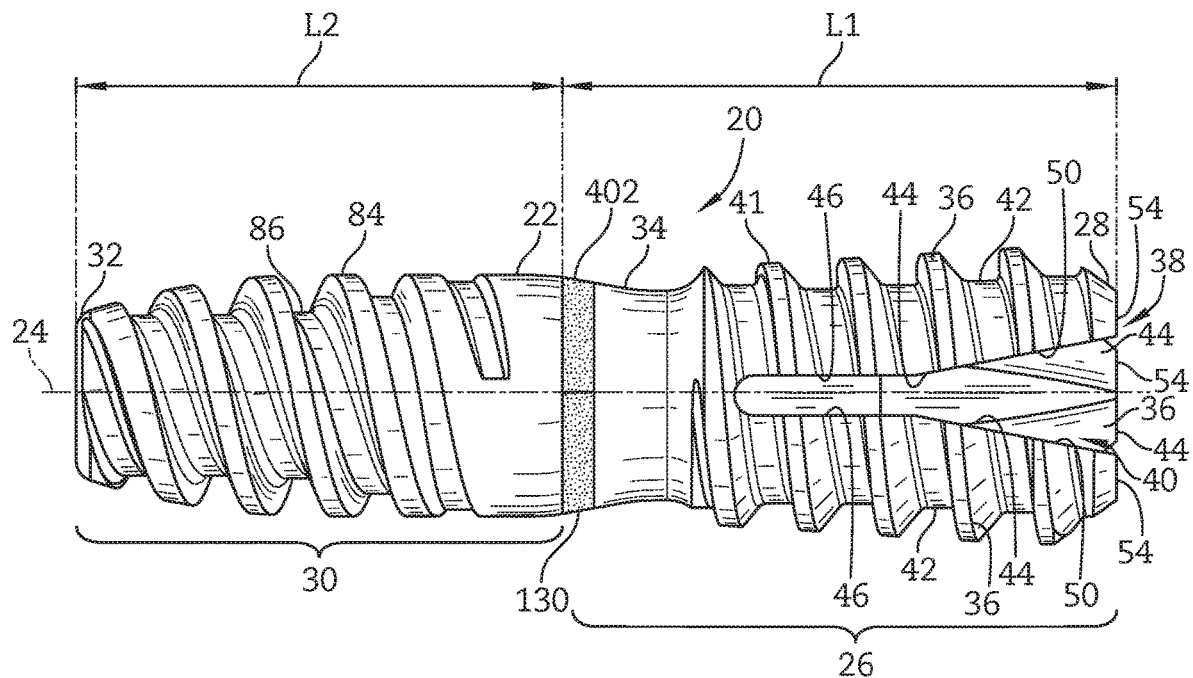
FIG. 2 is an elevational view of a first side of the implant of FIG. 1.
Figure 3:
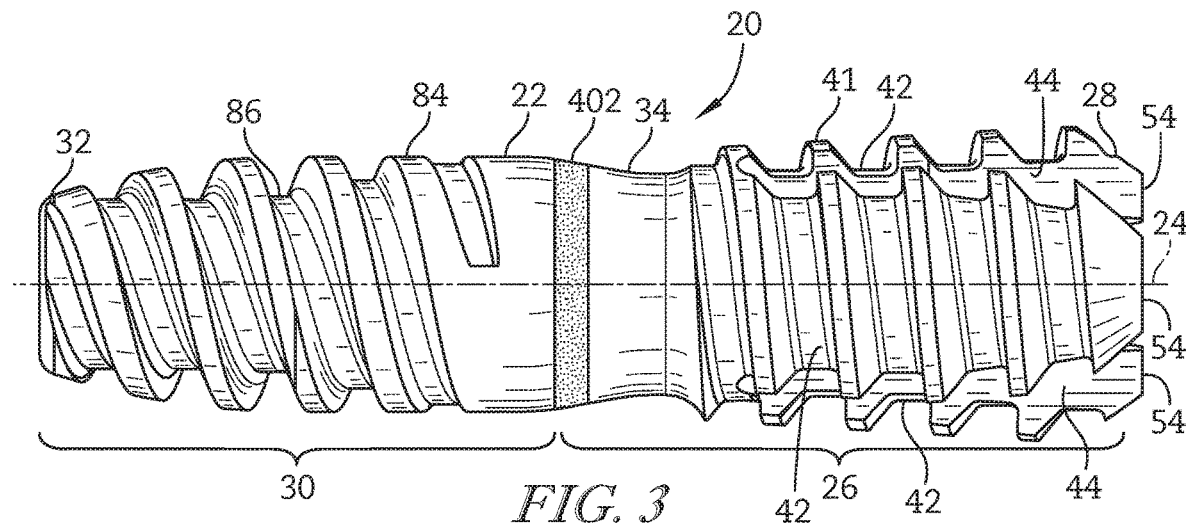
FIG. 3 is an elevational view of a second side of the implant of FIG. 1, wherein the second side is opposite the first side depicted in FIG. 2.
Figure 4:
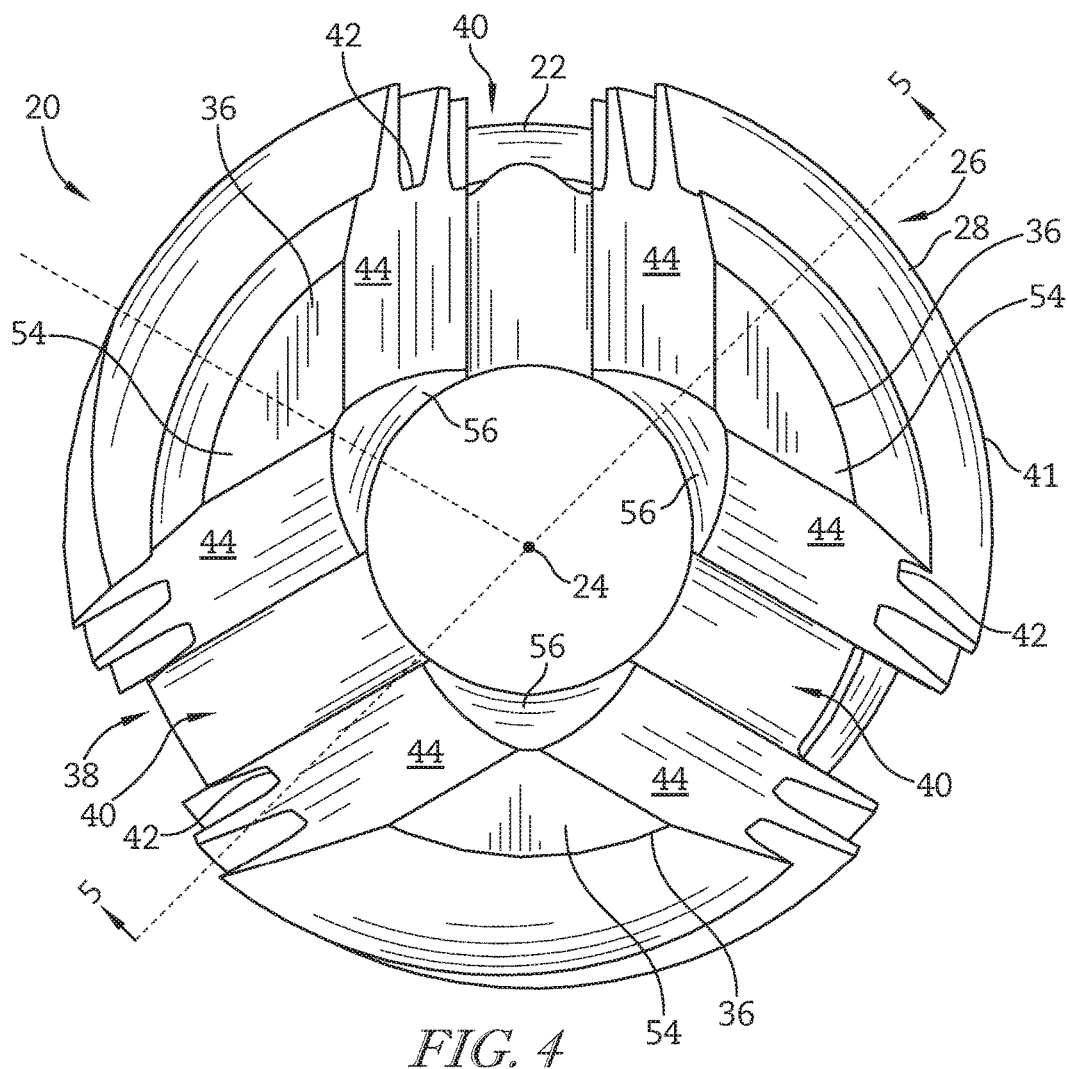
FIG. 4 is an elevational view of the first end of the implant of FIG. 1.
Figure 5:
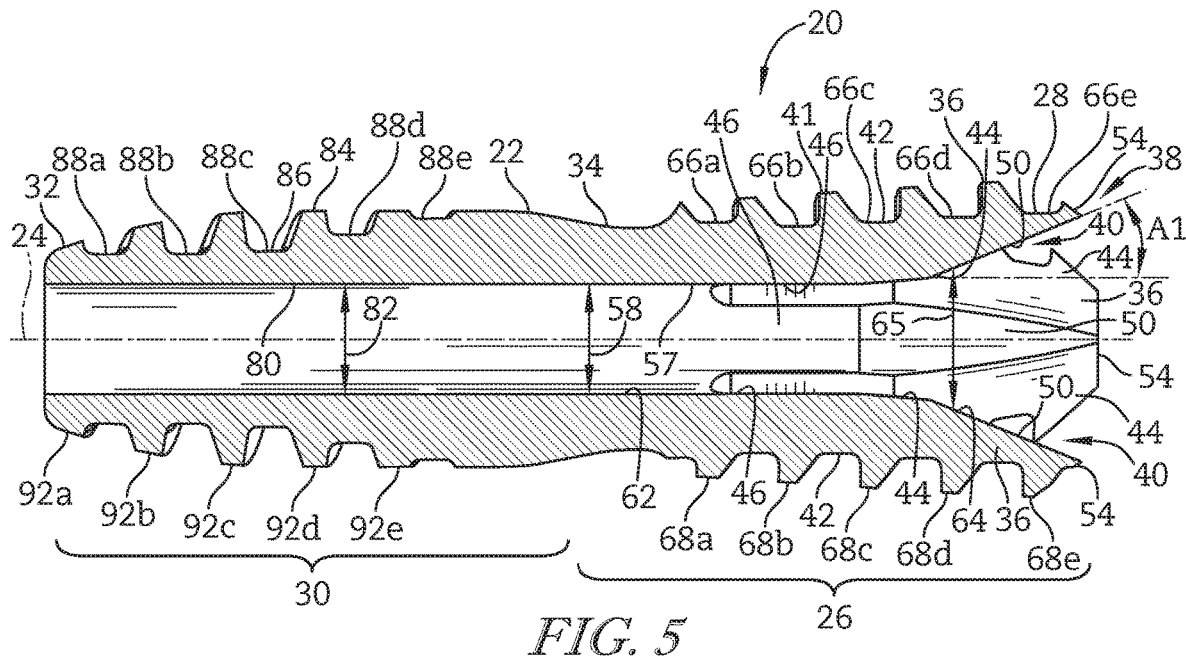
FIG. 5 is a cross-sectional view of the implant of FIG. 1 taken generally along the lines 5-5 of FIG. 4.
Figure 6:
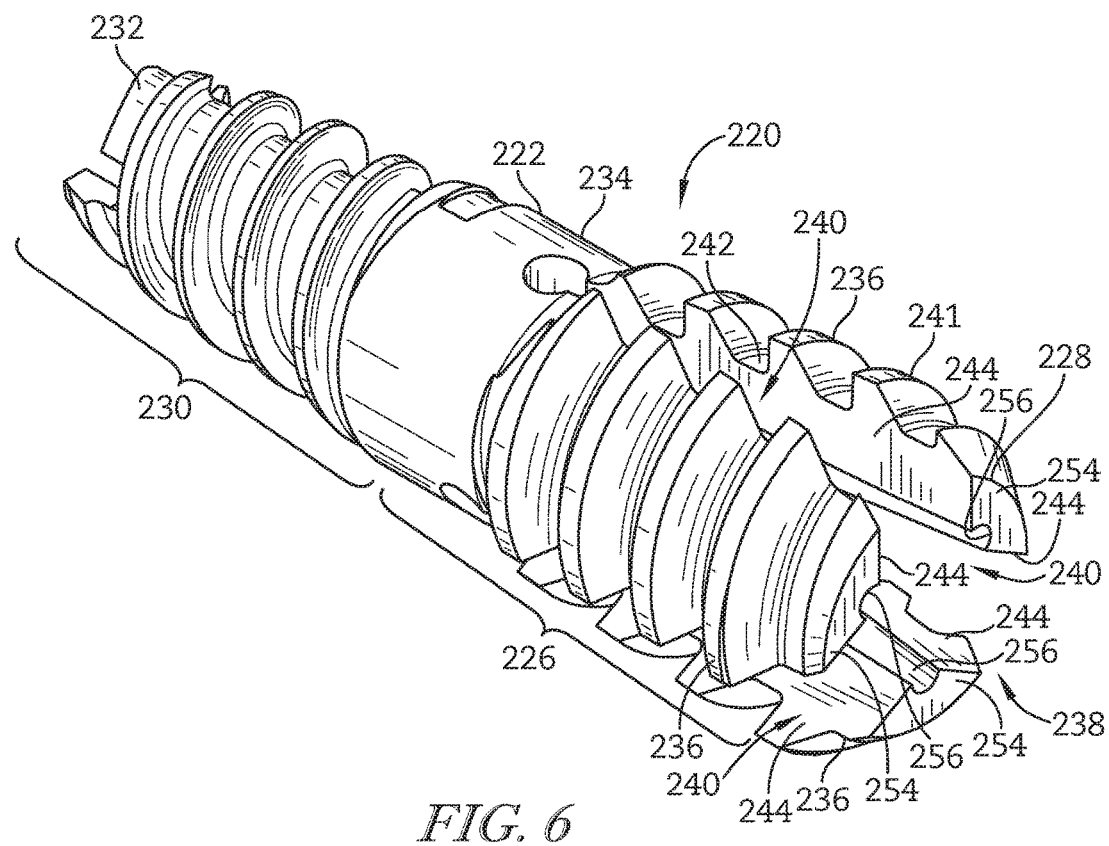
FIG. 6 is an isometric view of a second embodiment of an orthopedic implant taken generally from a first end of the implant.

As seen in FIGS. 1, 2, and 4, each of the arms 36 is separated from adjacent arms 36 by a channel 40. Helical threading 41 may be disposed about outer edges or surfaces 42 of each of the arms 36 and may continue between arms 36 (despite the existence of channels 40 therebetween). Each of the arms 36 is formed by opposing side edges 44 that, with side edges 44 of adjacent arms 36, form the channels 40. As seen in FIGS. 2 and 6, each side edge 44 is formed of a straight segment 46 that is generally parallel to a longitudinal axis 24 of the implant 20 and a tapered segment 50 that tapers outwardly from the straight segment 46 at an angle A1 of greater than 0 degrees to a tip forming a flattened edge 54. In an illustrative embodiment, the angle A1 may be between about 1 degree and about 15 degrees. In another illustrative embodiment, the angel A1 may be between about 3 degrees and about 10 degrees. In a further illustrative embodiment, the angel A1 may be about 7 degrees. As seen in FIG. 4, each arm 36 further includes a generally cylindrical inner edge 56 (FIG. 4) that tapers outwardly from an inner, generally cylindrical surface 57 of the proximal segment 26. The tapered segment 50 and the inner edge 56 are tapered to thin out the arms 36 to provide a desired stiffness and even stress distribution for each of the arms 36.

The use of three arms 36 provides more resistance to bending of the arms 36 along various axes that are perpendicular to the longitudinal axis 24. Less bending equates to higher contact forces and improved fixation. Three arms 36 also stabilize the bone in which implantation occurs more than two arms, since two arms leave a weak bending axis.

Currently, a number of hammertoe implant designs incorporate two spring arms for retention in the proximal phalanx, the middle phalanx, or both. Designs with two arms are intrinsically easier to manufacture through machining and may be easier to insert into the bone, as well. It has been discovered in the present invention that designs with multiple arms, for example, those with an odd number of arms, impart a strong advantage to implant fixation in the bone. Implant fixation into the bone is a common failure mode because bone in older hammertoe patients is oftentimes osteopenic and poorly supports an interface with the implant. The key to implant stability is the ability of the implant to uniformly impart stresses to the underlying bone. The loading vector for a hammertoe implant is predominantly in the dorsal-plantar direction as the foot moves through the gait cycle, however, complex tri-axial stresses also occur in all planes as the foot pushes laterally or moves over uneven surfaces. The objective of the implant designer should be to create a design that retains strength and fixation even in a tri-axial stress state.

Figure 18A:
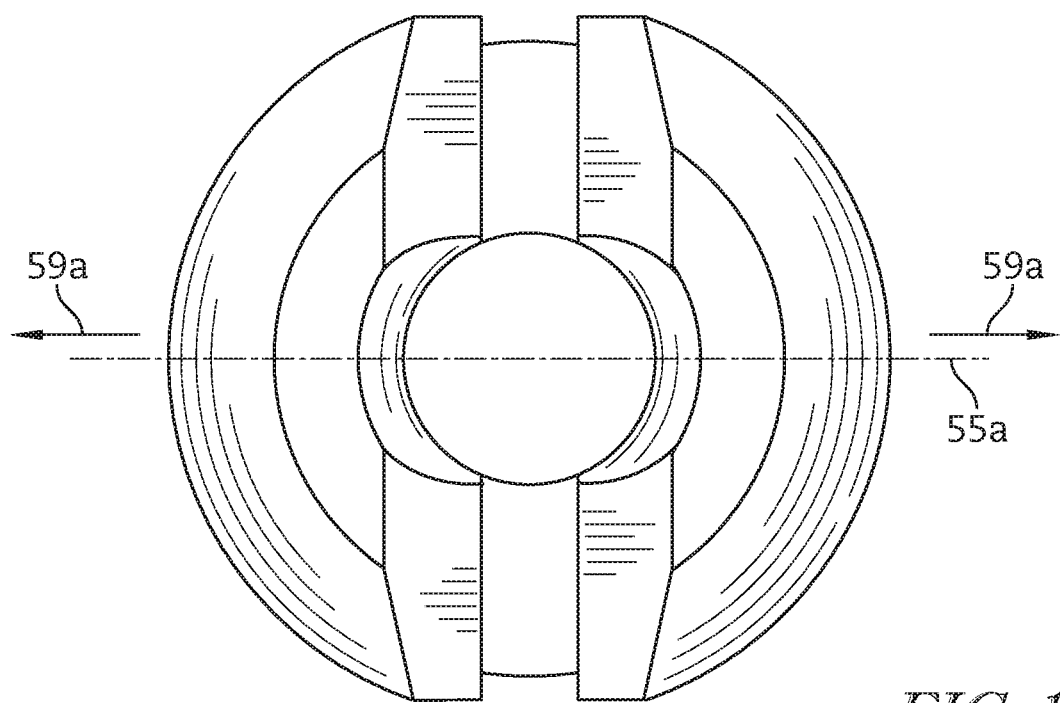
FIGS. 18A and 18B are views depicting bending axes for orthopedic implants having two and three arms, respectively.

A two-arm implant design, as seen in FIG. 18A, has a weak bending axis 55a on a plane of symmetry between the two arms. This weak axis 55a imparts a deficiency to the design in resisting tri-axial stresses, particularly when the dorsal-plantar loading vector is aligned perpendicularly to a vector of the arm spring force 59a. In this case, the spring arms contribute little to the stability of the implant in the bone.

Figure 18B:
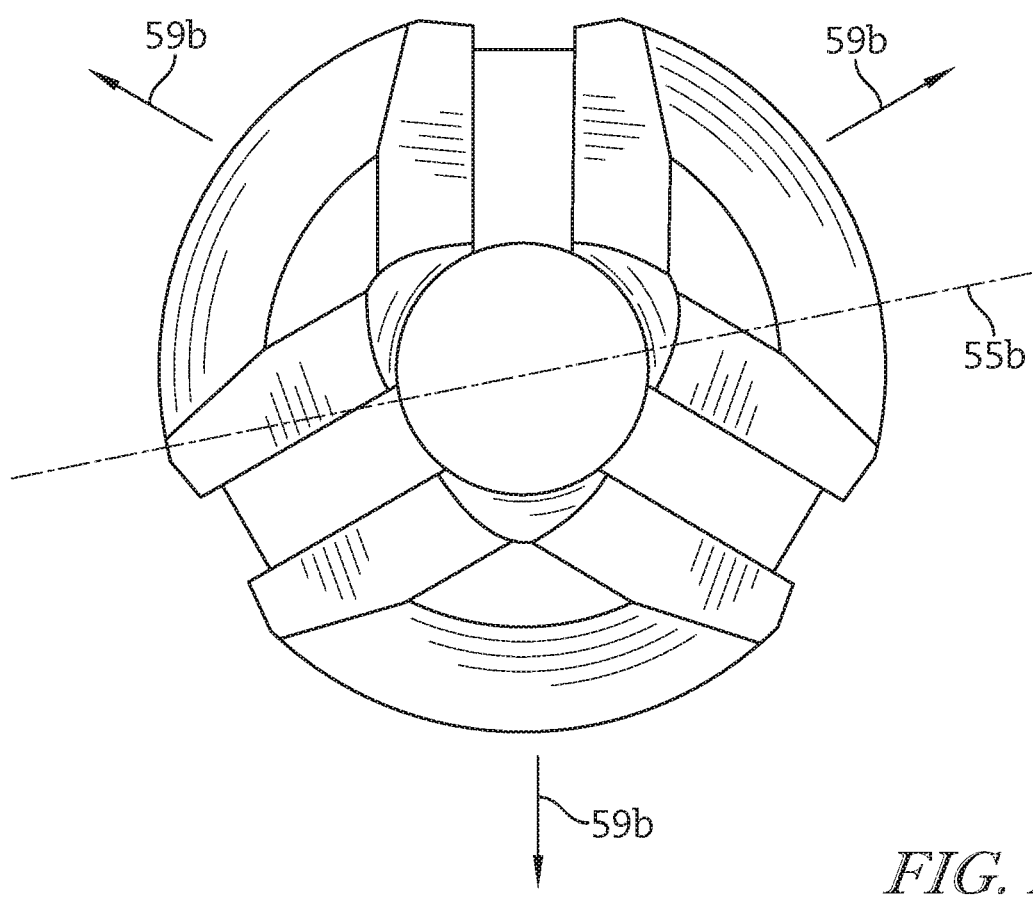

As seen in FIG. 18B, a three-arm implant design still has weak bending axis 55b, but the weak bending axis 55b is not as weak as the weak bending axis 55a of the two-arm design since there are now arms at more angular positions along a diameter of the implant. Even if a weak axis 55b of the implant is aligned with the dorsal-plantar loading vector, there are portions of the adjacent spring arms that directly contribute to resistance on the loading vector. This advantage is shared by all arm designs having three or more arms, although odd-numbered arm designs convey a particular evenness between the strong and weak axes. Additionally, with odd-numbered arm designs, the dorsal-plantar loading vector is not aligned perpendicularly to the vector of the arms spring force 59b. An additional advantage of a three-arm design is that it self-centers in a center of a hole in the bone in which it is implanted.

Referring to FIG. 6, the inner surface 57 of the proximal segment 26 has an inner diameter 58 that does not vary along a first section 62 that includes both the central, narrowed segment 34 and a portion of the arms 36. The inner surface 58 further includes a second section 64 that includes the generally cylindrical surface 57 of the arms 36 and which has a diameter 65 that increases along the longitudinal axis 24 from the central segment 34 toward the first end 28. The arms 36, as seen in FIG. 6, include outer edges 42 that, due to the helical threading 41, have minor diameters 66a-66e and major diameters 68a-68e. The minor diameters 66a-66e of the helical threading 41 may be constant in that the diameters thereof do not vary along a length of the threading 41. The major diameters 68a-68e of the helical threading 41 may increase from a first major diameter 68a closest the central segment 34 toward the first end 28 of the proximal segment 30. More particularly, a major diameter 68a of the threading 41 may be smaller than each of the other major diameters 68b-68e and the major diameters 68b-68e may each increase between the central segment 34 and the first end 28. An increasing major diameter 68a-68e maximizes bony contact during insertion of the second end 28 of the implant 20 into a proximal phalanx, as discussed in more detail below. In other illustrative embodiments, two or more consecutive or non-consecutive major diameters 68a-68e may be increasing between the major diameter 68a and the major diameter 68e and/or two or more consecutive or non-consecutive major diameters 68a-68e may be the same.

Referring again to FIG. 6, the distal segment 30 includes an inner cylindrical surface 80 having an inner diameter 82. The inner diameter 82 may be the same or different than the inner diameter 58 of the proximal segment 26. Helical threading 84 may be disposed on an outer surface 86 of all or a portion of the distal segment 30. As seen in FIG. 6, the helical threading 84 includes minor diameters 88a-88e and major diameters 92a-92e, wherein the minor diameters 88a-88e may increase along the longitudinal axis 24 of the implant 20 between the second end 32 and the first end 28. More particularly, a minor diameter 88a of the threading 84 may be smaller than each of the other minor diameters 88b-88e and the minor diameters 88a-88e may increase between minor diameter 88a and minor diameter 88e. Increasing minor diameters 88a-88e provide tactile feedback when implanting the distal segment 30 of the implant 20 into a middle phalanx, as discussed in greater detail below. In alternative illustrative embodiments, two or more consecutive or non-consecutive minor diameters 88a-88e may increase between minor diameter 88a and minor diameter 88e and/or two or more consecutive or non-consecutive minor diameters 88a-88e may be same. Major diameters 92a-92e of the helical threading 84 may increase in diameter from the major diameter 92a to the major diameter 92e or the major diameters 92a-92e may be the same. Still alternatively, two or more consecutive or non-consecutive major diameters 92a-92e may be increasing between the major diameters 92a and the major diameter 92e and/or two or more consecutive or non-consecutive major diameters 92a-92e may be the same.

While a particular number of threads are depicted for the threading 41 and 84, any number of threads may be present depending on a particular application for the implant 20.

A second embodiment of an orthopedic implant 220 suitable for treatment and correction of hammertoe is depicted in FIGS. 6-11. The implant 220 generally includes a pin-shaped body 222 extending along a longitudinal axis 224 and further includes a proximal segment 226 terminating in a first end 228 and a distal segment 230 terminating in a second end 232. The proximal and distal segments 226, 230 may be integral with one another and joined at a central, cylindrical flattened segment 234 of the implant 220. The proximal segment 226 of the body 222 may generally comprise the central flattened segment 234 and three arms 236 that form a barbed anchor 238 and which extend away from the central, flattened segment 234.

Figure 7:
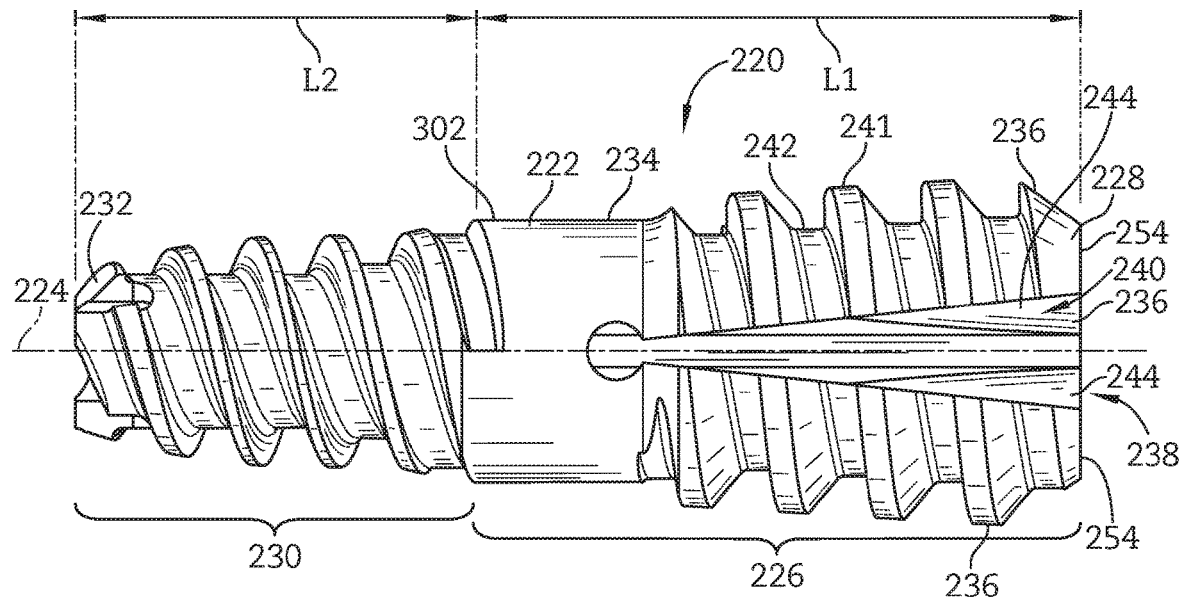
FIG. 7 is an elevational view of a first side of the implant of FIG. 6.
Figure 8:
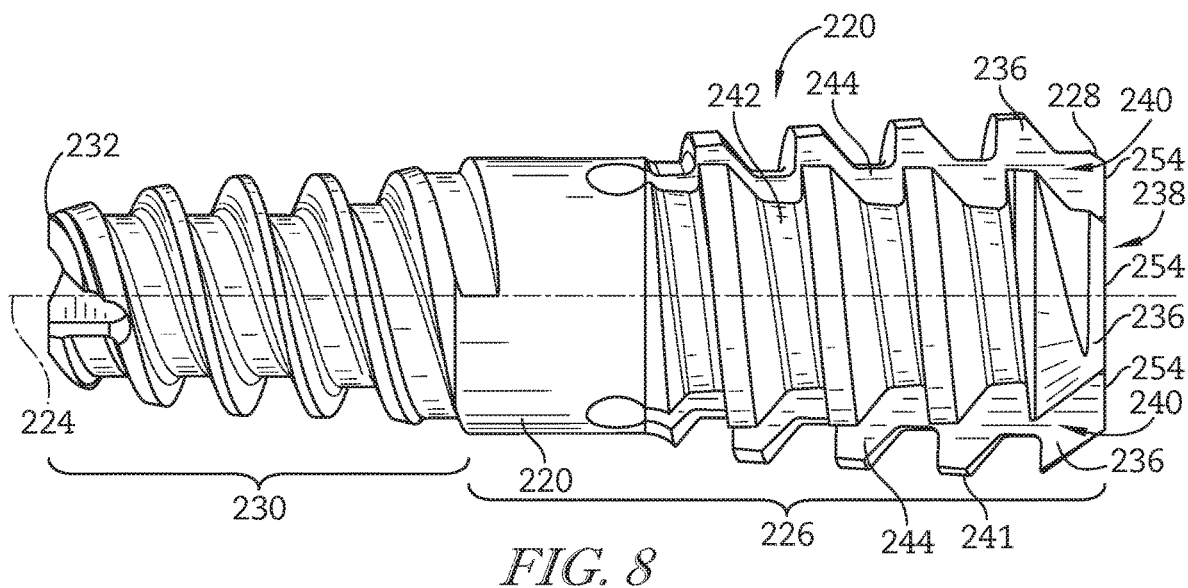
FIG. 8 is an elevational view of a second side of the implant of FIG. 6, wherein the second side is opposite the first side depicted in FIG. 7.
Figure 9:
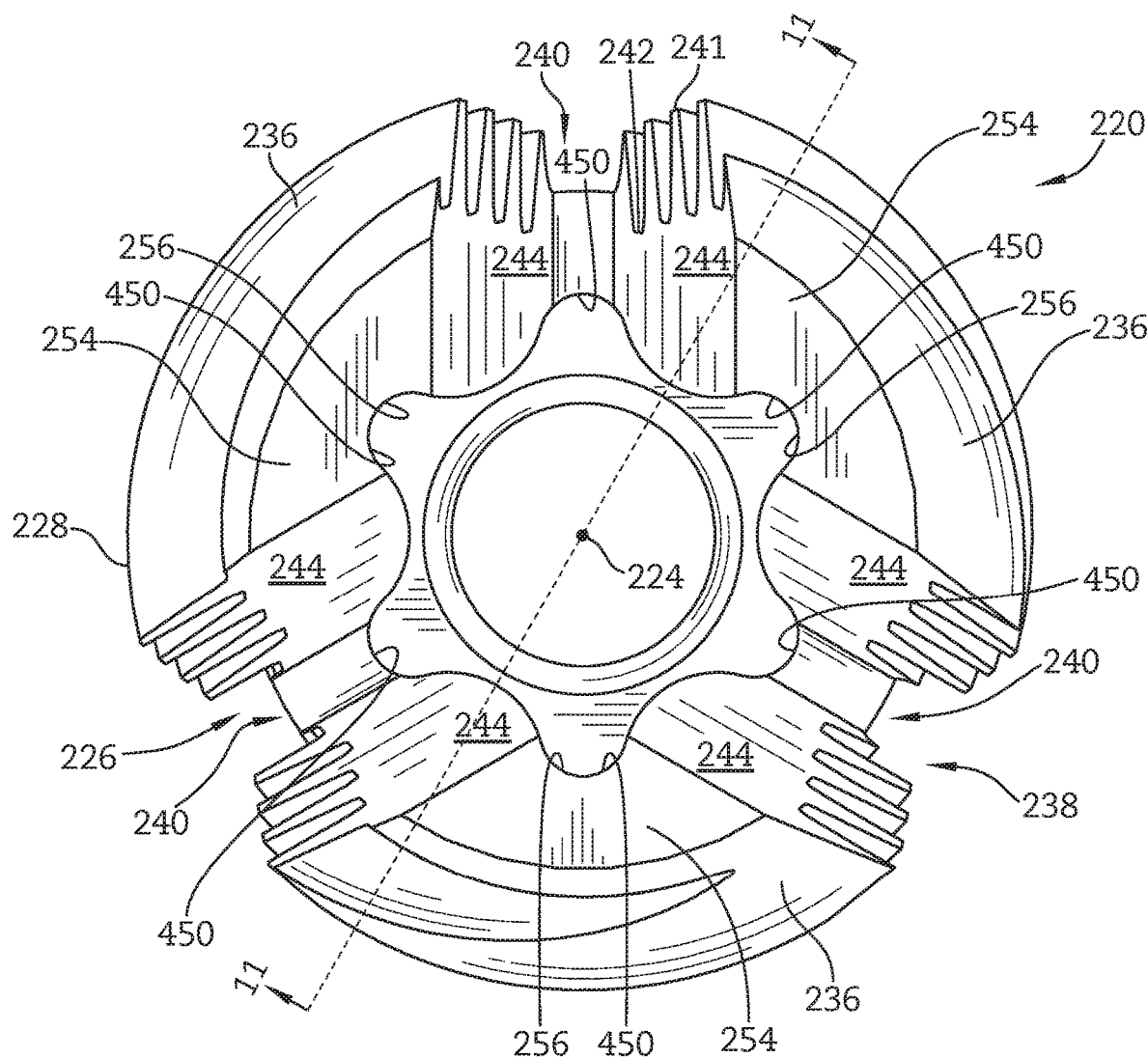
FIG. 9 is an elevational view of the first end of the implant of FIG. 6.
Figure 10:
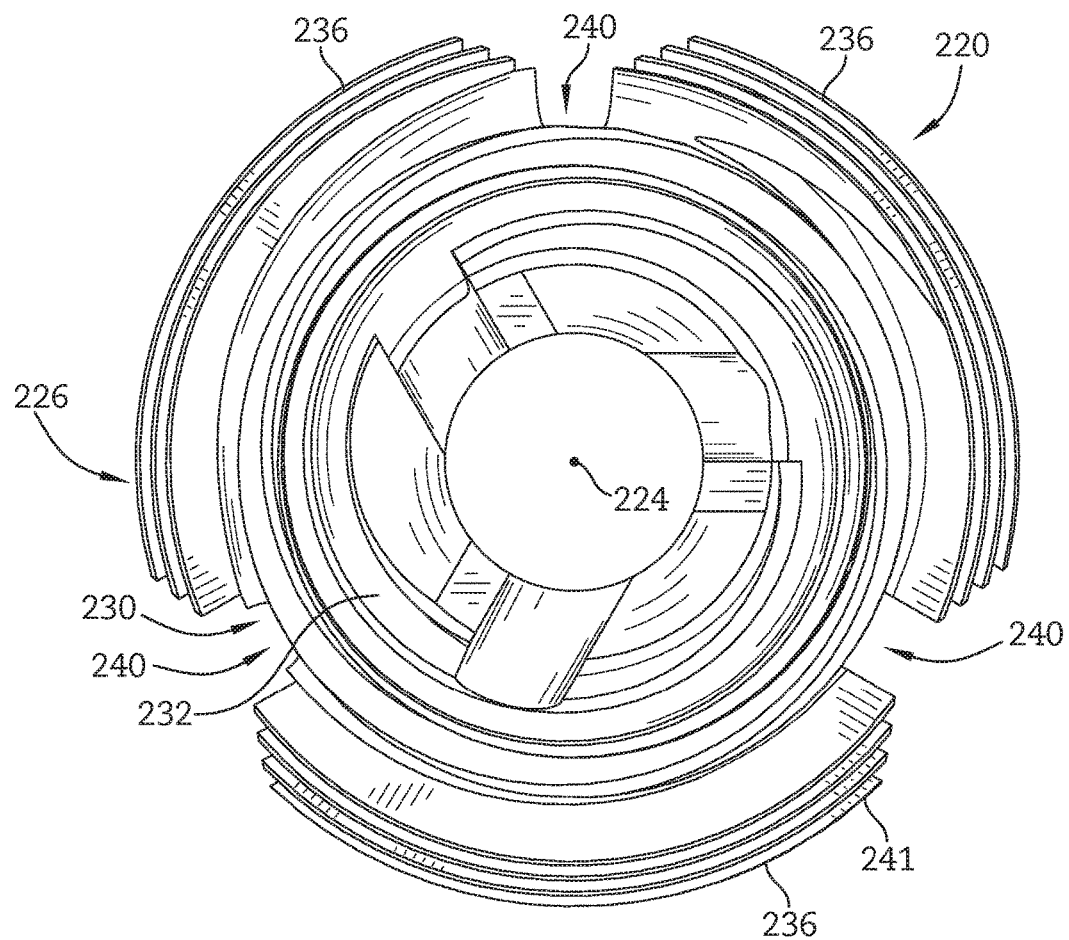
FIG. 10 is an elevational view of a second end of the implant of FIG. 7, wherein the second end is opposite the first end.
Figure 12:
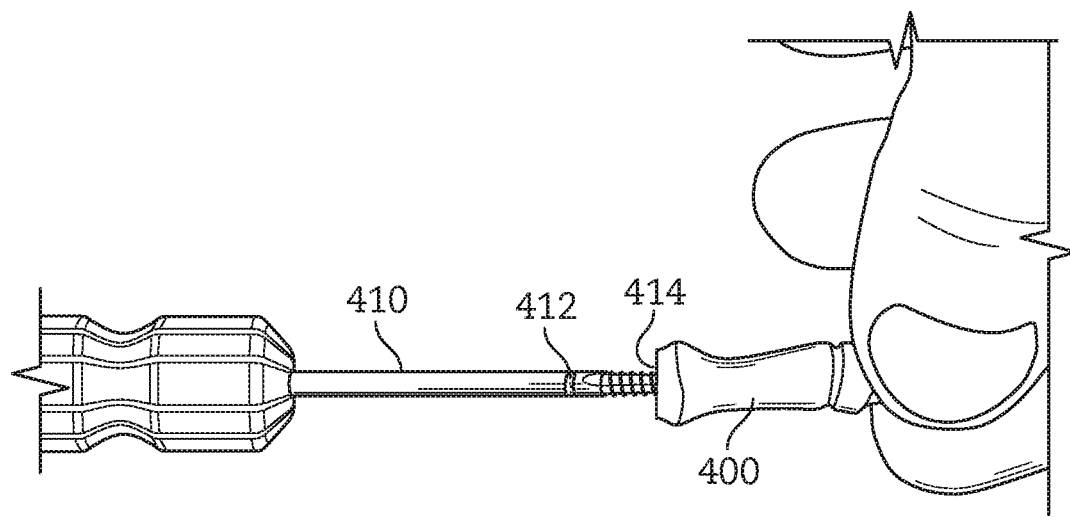
FIG. 12 is a view depicting a tap advanced over a distal Kirschner wire (K-wire) into a middle phalanx of a patient during a first method of implantation of an orthopedic implant disclosed herein.

As seen in FIGS. 5, 6, 7, and 9, each of the arms 236 is separated from adjacent arms 236 by a channel 240. Helical threading 241 may be disposed about outer edges or surfaces 242 of each of the arms 236 and may continue between arms 236 (despite the existence of channels 240 therebetween). Each of the arms 236 is formed by opposing side edges 244 that, with side edges 244 of adjacent arms 236, form the channels 240. As seen in FIGS. 7 and 12, each side edge 244 tapers outwardly at an angle A2 of greater than 0 degrees to a tip forming a flattened edge 254. In an illustrative embodiment, the angle A2 may be between about 1 degree and about 15 degrees. In another illustrative embodiment, the angel A2 may be between about 3 degrees and about 10 degrees. In a further illustrative embodiment, the angel A2 may be about 7 degrees. As seen in FIGS. 6 and 10, each arm 236 further includes an inner, generally cylindrical edge 256 that tapers outwardly from an inner, generally cylindrical surface 258 of the proximal segment 226.

Figure 11:
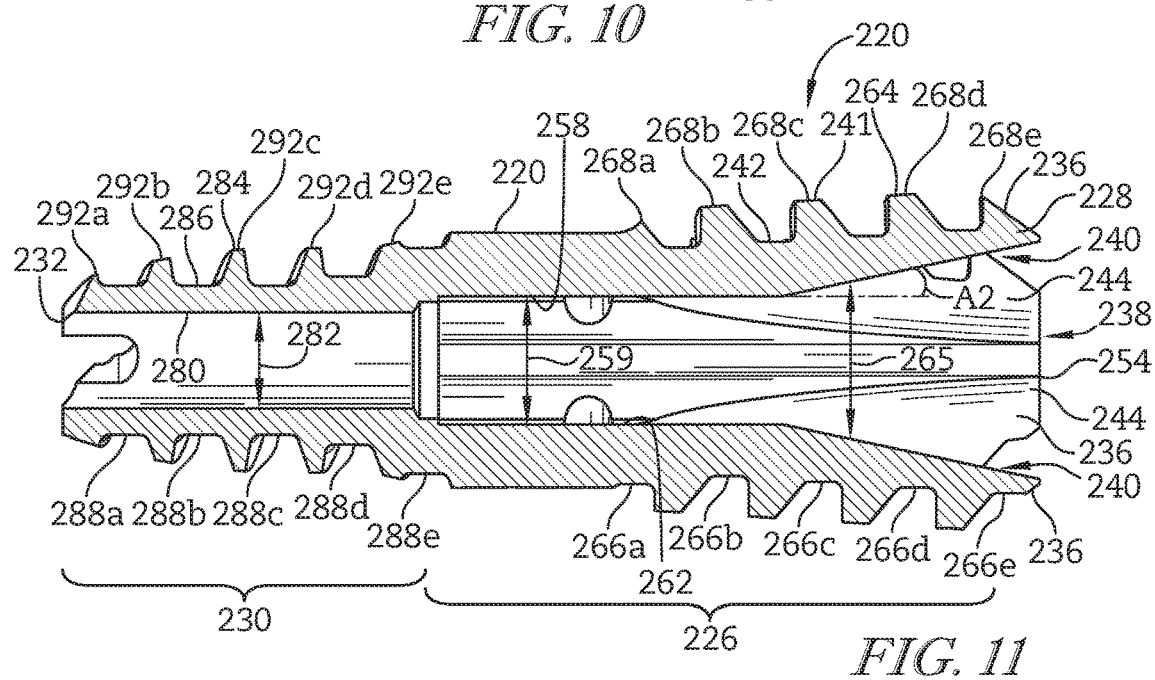
FIG. 11 is a cross-sectional view of the implant of FIG. 6 taken generally along the lines 11-11 of FIG. 9.

Referring to FIG. 11, the inner surface 258 of the proximal segment 226 has an inner diameter 259 that may not vary along a first section 262 and that may include both the central segment 234 and a portion of the arms 236. The inner diameter 258 may further include a second section 264 that includes at least a portion of the arms 236 and which has a diameter 265 that increases along the longitudinal axis 224 from the central segment 234 toward the first end 228. The arms 236, as seen in FIG. 11 include helical threading 241 that has minor diameters 266a-266e and major diameters 268a-268e. The minor diameters 266a-266e of the helical threading 41 may be constant in that the diameters thereof do not vary along a length of the threading 241 or the minor diameters 266a-266e may have different or varying diameters. The major diameters 268a-268e of the helical threading 41 may be constant in that the diameters thereof do not vary along a length of the threading 241 or the major diameters 268a-268e may have different or varying diameters. In illustrative embodiments and similar to the embodiment of FIGS. 1-5, the major diameters 268a-286e may increase from a first major diameter 268a closest the central segment 234 toward the first end 228 of the proximal segment 230. In other illustrative embodiments, two or more consecutive or non-consecutive major diameters 268a-268e may be increasing between the major diameter 268a and the major diameter 268e and/or two or more consecutive or non-consecutive major diameters 268a-268e may be the same.

Referring again to FIG. 11, the distal segment 230 includes an inner cylindrical surface 280 having an inner diameter 282. The inner diameter 282 may be constant or may vary along the longitudinal axis 224. The inner diameter 282 may be the same as or less than the inner diameter 259 of the proximal segment 226. Helical threading 284 may be disposed on an outer surface 286 of all or a portion of the distal segment 230. As seen in FIG. 11, a minor diameter 288a-288e of the helical threading 284 may be the same for each thread or may increase along the longitudinal axis 224 of the implant 220 from the second end 232 toward the first end 228, as discussed above with respect to the embodiment of FIGS. 1-5. In other illustrative embodiments, two or more consecutive or non-consecutive minor diameters 288a-288e may be increasing between the minor diameter 288a and the minor diameters 288e and/or two or more consecutive or non-consecutive minor diameters 288a-288e may be the same.

Major diameters 292a-292e of the helical threading 284 may increase in diameter from the major diameter 292a to the major diameter 292e or the major diameters 292a-292e may be the same. Still alternatively, two or more consecutive or non-consecutive major diameters 292a-292e may be increasing between the major diameters 292a and the major diameter 292e and/or two or more consecutive or non-consecutive major diameters 292a-292e may be the same.

While a particular number of threads are depicted for the threading 241 and 284, any number of threads may be present depending on a particular application for the implants 20, 220.

Figure 13:
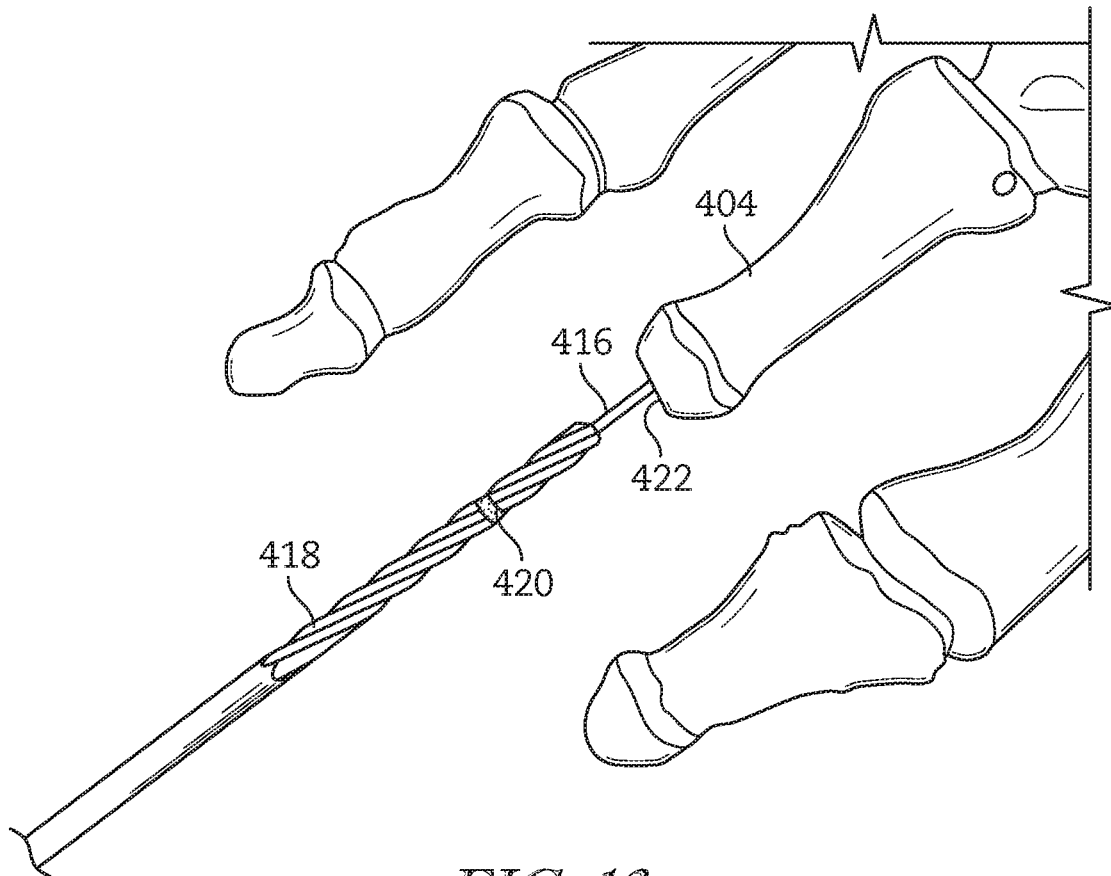
FIG. 13 is a view depicting a proximal K-wire inserted into a center of a proximal phalanx of a patient and a drill advanced over the K-wire during the first method of implantation of an orthopedic implant.

Implantation of the implants 20, 220 will now be discussed in detail. Prior to implantation, the proximal interphalanxal (PIP) joint of the patient is opened using, for example, a dorsal approach. A head of a proximal phalanx 104 of the patient is prepared by reaming until bleeding bone is reached, for example, using a proximal phalanx reamer and a base of a middle phalanx 100 of the patient is also reamed until bleeding bone is reached, for example, using a middle phalanx reamer. Once the middle phalanx 400 is reamed, a distal K-wire may be inserted into a center of the middle phalanx 400. As seen in FIG. 12, tap 410 of the appropriate size 410 is selected for the desired implant size and, using firm axial pressure, the tap 410 is advanced over the distal K-wire into the middle phalanx 100 until a laser line 412 on the tap 410 is level with an outer surface 414 of the middle phalanx 400. A proximal K-wire 416 may be inserted into a center of the proximal phalanx 404, as seen in FIG. 13. In an illustrative embodiment, the K-wire 416 may be introduced at a 10 degree angle plantar to a medial axis of the proximal phalanx 404. An appropriate drill size may be selected and advanced over the K-wire 416 into the proximal phalanx 404 until a laser line 420 on the drill 418 is level with an outer surface 422 of the proximal phalanx 404, as seen in FIG. 13, and the proximal K-wire 416 may be removed after drilling.

Figure 14A:
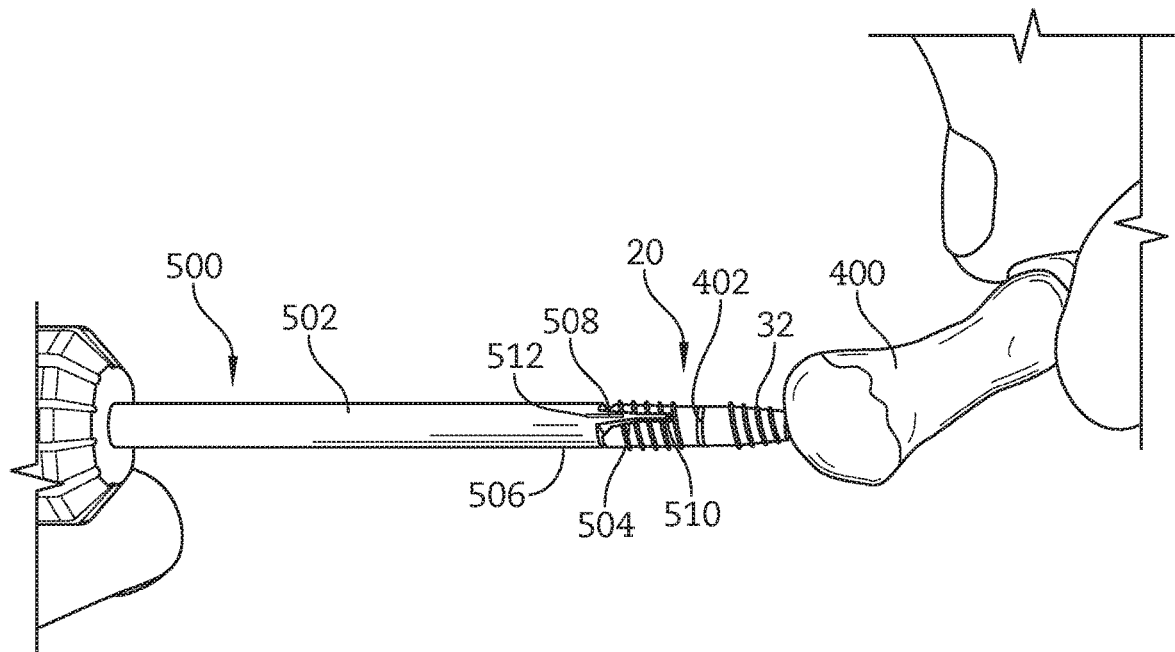
FIG. 14A is a view depicting a second end of a distal segment of an orthopedic implant threaded into the middle phalanx of a patient during the first method of implantation of an orthopedic implant utilizing an implantation tool.

The second end 32, 232 of the distal segment 30, 230 of either implant 20, 220 is threaded into the middle phalanx 400 of the patient, as seen in FIG. 14A, using an implantation tool 500, until an increase in torque indicates firm seating of the implant 20, 220. Additionally, an outer edge of the middle phalanx 400 may be aligned with a laser line 402 positioned between the proximal and distal segments 26 or 226, 30 or 230 and should be facing dorsally. The laser line 402 is formed of one or more of a black burn, engraving, one or more dyes, or any other suitable substance capable of creating a line, marker, or other indicator. The laser line 402 provides guidance to a surgeon or other healthcare professional such that the distal segment 30, 230 of the implant 20, 220 is threaded into the middle phalanx 400 to an optimal or ideal depth. The laser lines on the tap 410 and the drill 418 additionally prepare the bone for insertion of the implant 20, 220 to an appropriate depth.

Figure 14B:
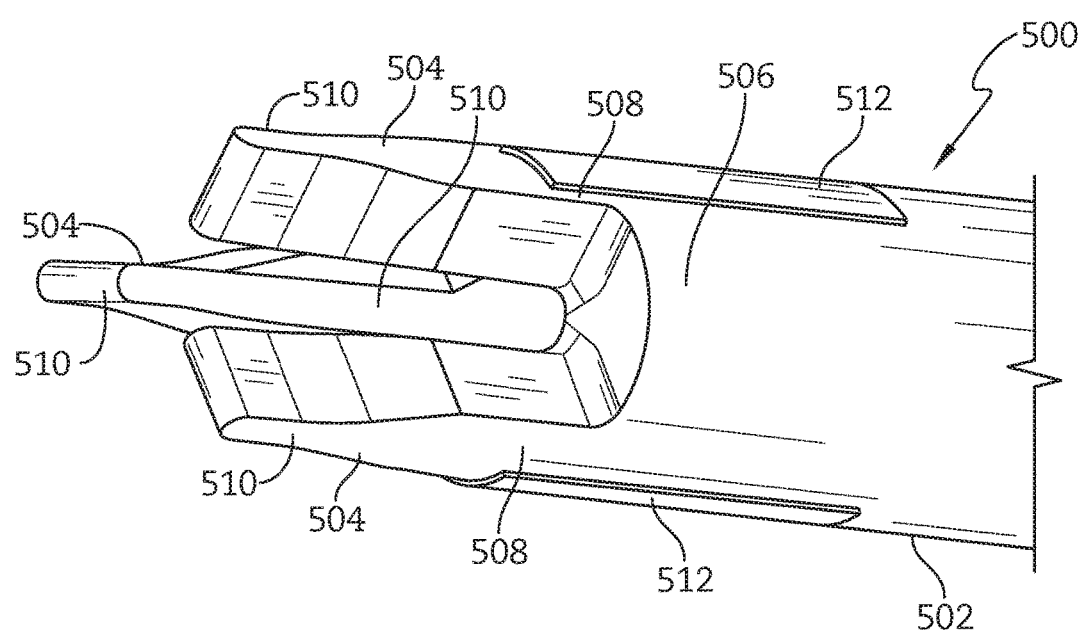
FIG. 14B is a perspective view of a drive end of the implantation tool shown in use in FIG. 14A, wherein the implantation tool is utilized to thread the distal segment of the orthopedic implant into the middle phalanx.

The implantation tool 500, as best seen in FIG. 14B, may include a generally cylindrical body 502, although, the body 502 need not be cylindrical. Three arms 504 extend outwardly from a first end 506 of the body 502. Each of the arms 504 includes a wider based 508 that tapers into a narrowed tip 510. The arms 504 are sized and shaped to be complementary to and fit within the channels 40, 240 formed by the arms 36, 236 of the implant 20, 220, as seen in FIG. 14A. In illustrative embodiments, the implantation tool 500 may retain the implant 20, 220 on the first end 506 by, for example, an interference fit. In other illustrative embodiments, the implantation tool 500 may fit within the implant 20, 220, but may not retain the implant 20, 220 on the first end 506.

As may be seen in FIG. 14A, an outer diameter of the arms 504 of the implantation tool 500 is fully within an outer or major diameter of the threads 68a-68e, 268a-268e. Each of the arms 504 may also include a laser mark 512 that denote which way the implant arms 36, 236 are oriented. As one skilled in the art will understand, if an implant includes more than three arms/three recesses, the implantation tool 500 may include a similar number of arms.

Figure 15:
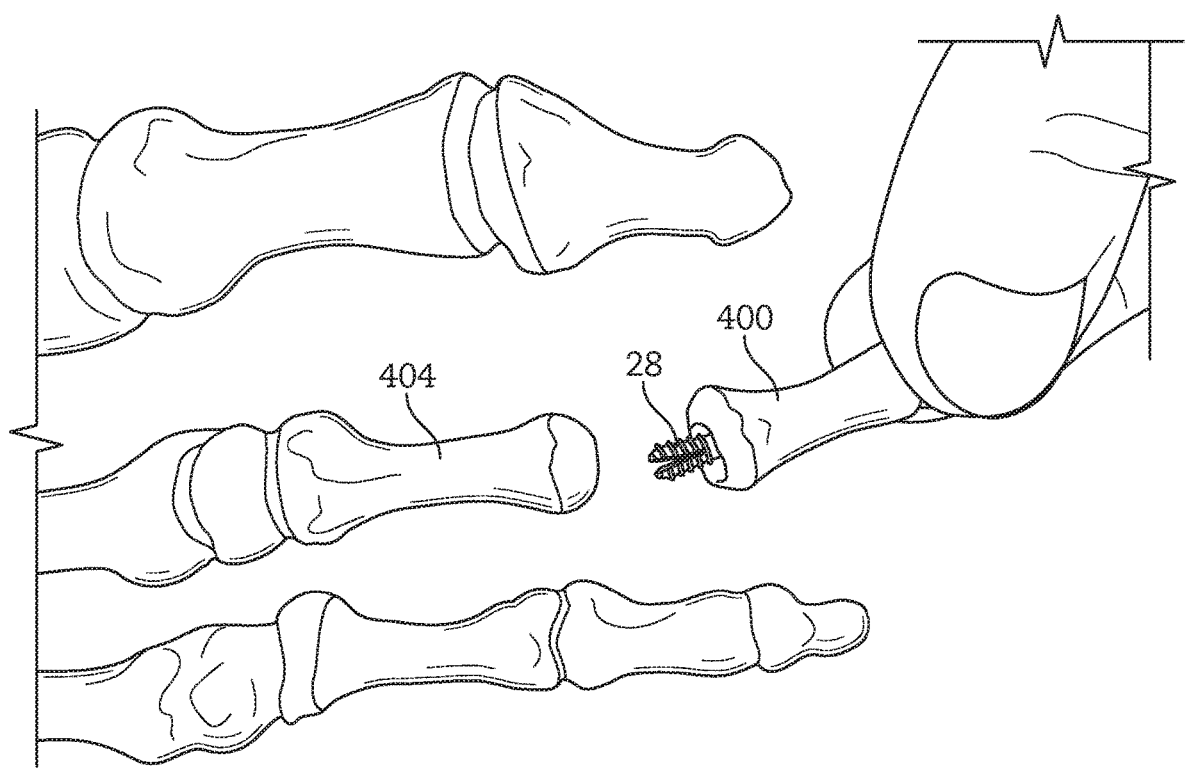
FIG. 15 is a view depicting insertion of a barbed anchor disposed at a first end of a proximal segment of an orthopedic implant into a pre-drilled hole in the proximal phalanx of the patient during the first method of implantation of an orthopedic implant.
Figure 16:
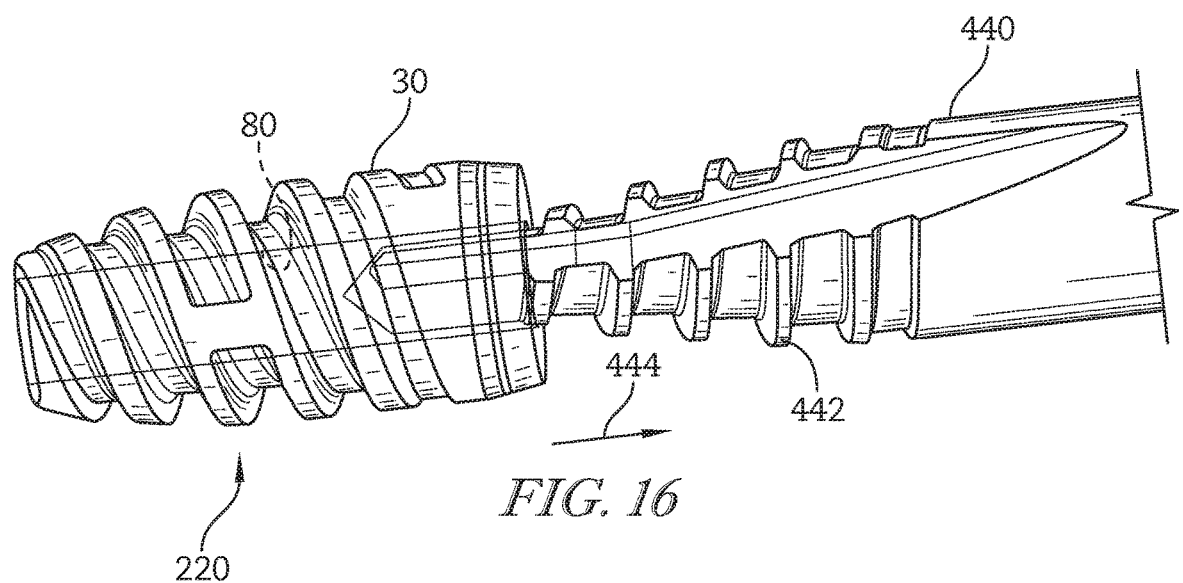
FIG. 16 is a view depicting a method of removing a distal segment of an orthopedic implant in which a threaded tool is utilized to tap an inner surface of the distal segment.
Figure 17:
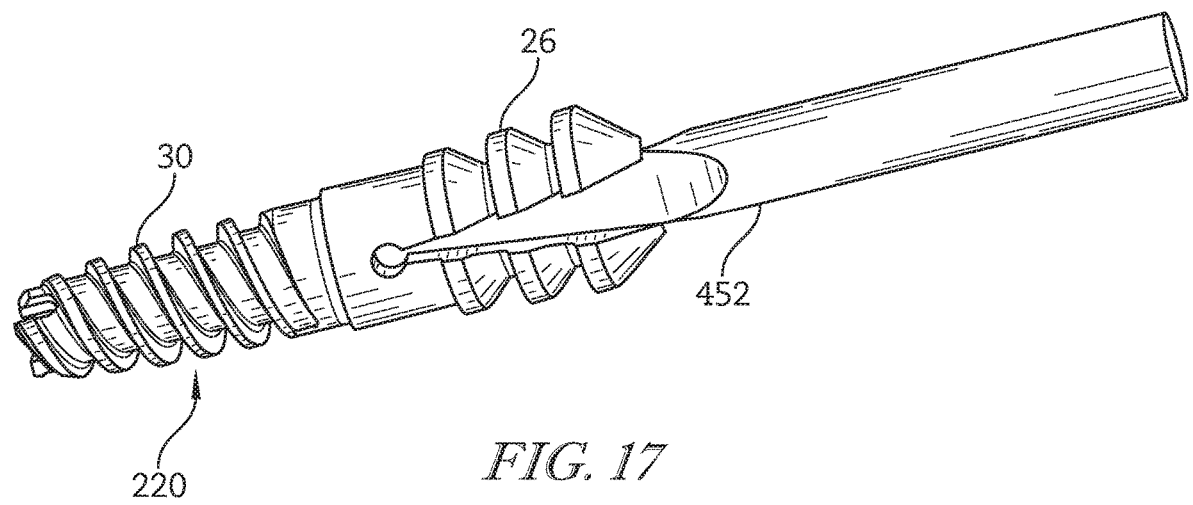
FIG. 17 is a view depicting a method of removing an orthopedic implant in which a tool having a drive features is utilized in combination with a complementary drive feature within a proximal segment of an orthopedic implant to remove the implant.

After the distal segment 30, 230 is implanted within the middle phalanx 400 and the distal K-wire 416 is removed, the proximal segment 26, 226 of the implant 20, 220 is aligned with a proximal phalanx 404 of the patient. More specifically, the barbed anchor 38, 238 at the first end 28, 228 of the proximal segment 26, 226 is aligned with and inserted into the pre-drilled hole in the proximal phalanx 404, as seen in FIG. 15. The proximal segment 26, 226 is thereafter pressed into the proximal phalanx 404. Once both the proximal and distal segments 26 or 226, 30 or 230 are implanted within the proximal and middle phalanges 404, 400, respectively, a typical surgical procedure is used to close the patient.

Oftentimes, implants, such as implant 20, 220 or any of the implants disclosed herein, must be removed and replaced (during, for example, a revision surgical procedure). It can be very difficult to remove the distal and/or proximal segments 30 or 230, 26 or 226 from the middle and proximal phalanges 400, 404, respectively. The implant 20, 220 may be provided with features that allow for easier removal of the implant 20, 220 from the middle and proximal phalanges 400, 404. More particularly, in illustrative embodiments, the implant 20, 220 may be manufactured of a polymeric material, for example, ultra-high molecular weight polyethylene (UHMWPE), polyetheretherketone (PEEK), or any other suitable polymeric material. The central segment 34, 234 of the implant 20, 220 may be cut to sever the proximal and distal segments 26 or 226, 30 or 230 from one another. In illustrative embodiments, the central segment 34, 234 may be cut at a point 130 adjacent the distal segment 30, 230.

In illustrative embodiments, once the implant, for example, the implant 20, is severed, a tool 440 that is made of a high-strength material, for example, stainless steel, having threading 442 may be threaded into the distal segment 30. In illustrative embodiments, the threading 442 on the tool 440 taps out the inner cylindrical surface 80 of the distal segment 30 such that opposing threads are created therein. Once the tool 440 is threaded a sufficient distance into the distal segment 30, the tool 440 may be threaded or pulled in a direction 444 opposite the direction of threading to remove the distal segment 30 from the middle phalanx 400. In a similar manner, the tool 440 may be threaded into the proximal segment 26, for example, such that the threading 442 on the tool 440 taps out an inner surface 446 of the central segment 34 and/or the proximal segment 26, thereby creating opposing threads therein. Once the tool 440 is threaded a sufficient distance into the proximal segment 26, the tool 440 may be threaded or pulled in a direction opposite the direction of threading to remove the proximal segment 26 from the proximal phalanx 404.

In other illustrative embodiments, the implant, for example, the implant 220, may include a proximal segment 226 having an internal drive feature 450 (see FIG. 9) that mates with a tool 452 such that, upon rotation of the tool 452, the distal segment 230 may be threaded out of the bore in which it was implanted. In the illustrative embodiment, the drive feature 450 may be comprised of a hexalobe bore formed by the cylindrical inner edge 256 that form semi-cylindrical channels and portions of the central segment 34 that form semi-cylindrical channels. Alternatively or additionally, the drive feature 450 may include any suitable feature(s) or geometry(ies) configured to accept a tool and allows for rotation of the implant 220 using the tool 452. While six semi-cylindrical channels are depicted in FIG. 9, any suitable number of semi-cylindrical channels may be utilized.

Any of the implants disclosed herein may be manufactured in different sizes, for example, for differently-sized phalanges of the same foot or phalanges of persons with differently-sized feet, toes, and/or phalanges. In an illustrative embodiment, three or more differently-sized implants may be provided, for example, small, medium, and large implants or small, medium, large, and extra-large implants. In an illustrative embodiment with small, medium, and large implants, an overall length of the small implant may be 13 millimeters, a proximal length L1 may be 7 millimeters, and a distal length L2 may be 6 millimeters. Similarly, an overall length of the medium implant may be 14 millimeters, the proximal length L1 may be 7 millimeters, and the distal length L2 may be 7 millimeters. Still further, an overall length of the large implant may be 15 millimeters, the proximal length L1 may be 7 millimeters, and the distal length may be 8 millimeters. In other embodiments, the overall length of one or more implants may be between about 5 millimeters and about 20 millimeters.

Any of the implants disclosed herein may be manufactured of one or more of metal, ultra-high molecular weight polyethylene (UHMWPE), ceramic, polyetheretherketone (PEEK), or any other suitable material or materials.

While the implants disclosed in detail herein are discussed as being suitable for treatment and correction of hammertoe, the implants disclosed herein may be utilized for treatment and/or correction of other conditions, for example, other conditions in the foot or hand and/or conditions related to other joints.

Any one or more features of any of the implant disclosed herein may be incorporated (alone or in combination) into any of the other implants disclosed herein.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There are a plurality of advantages of the present disclosure arising from the various features of the apparatus, systems, and methods described herein. It will be noted that alternative embodiments of the apparatus, systems, and methods of the present disclosure may not include all of the features described yet still benefit from at least some of the advantages of such features. Those of ordinary skill in the art may readily devise their own implementations of the apparatus, systems, and methods that incorporate one or more of the features of the present disclosure.

The invention claimed is:

1. A method for implanting an orthopedic implant, comprising the steps of:
   inserting three circumferentially spaced apart arms extending from a body of an orthopedic implantation tool into respective recesses of the orthopedic implant, the body defining a longitudinal axis and each of the arms including:
- a first surface extending from the body and within a first plane parallel to the longitudinal axis, and
- a second surface distal to and extending distally from the first surface, the second surface being within a second plane transverse to the longitudinal axis,
- wherein each of the first and second surfaces extends across a full width of the arm defined within a plane extending radially from the longitudinal axis; and rotating the arms of the implantation tool to thread the implant into a bone.

2. The method of claim 1, wherein the arms of the tool are rotated until a laser line on the implant meets with a surface of the bone.

3. The method of claim 1, further comprising rotating the body of the tool to rotate the arms of the tool.

4. The method of claim 1, wherein each of the tool arms is inserted between respective sets of two circumferentially spaced apart arms of the orthopedic implant when the tool arms are inserted into the orthopedic implant.

5. The method of claim 4, wherein each of the arms of the tool include a base and a tip that is attached to and thinner than the base, wherein the respective sets of two circumferentially spaced apart arms of the orthopedic implant each define a semi-cylindrical channel, and wherein the tip of each arm is complementary to each semi-cylindrical channel and the base is complementary to a surface wider than each semi-cylindrical channel.

6. The method of claim 1, wherein the bone is a phalanx.

7. The method of claim 1, wherein each of the arms of the implant includes a third surface within a third plane, the third plane being transverse to the second plane and the third surface being distal to the second surface, the third surface further extending from the second surface along a full width of the second surface.

8. A method for implanting an orthopedic implant, comprising the steps of:
- inserting three tool arms extending from a tool body of an orthopedic implantation tool into the implant,
  - wherein each of the tool arms defines a respective tip spanning a full width of the respective tool arm,
  - wherein the respective widths are defined along respective central planes through the respective tool arms that extend radially from the center of the implantation tool,
  - wherein a distal end of each of the tool arms is spaced apart from the distal ends of each of the other tool arms and each of the tool arms is configured for fitting within a respective recess of the implant,
  - wherein each tool arm includes a side having a plurality of surfaces defining a set of planes, each of the planes of the set of planes of the side being parallel to or forming a different angle with respect to the central plane of the respective tool arm than the other planes of the set of planes; and
- rotating the arms of the implantation tool to thread the implant into a bone.

9. The method of claim 8, further comprising:
- mating the arms of the implantation tool with a first end of the implant; and
- driving a second end of the implant opposite the first end into a middle phalanx.

10. The method of claim 9, wherein each of the tool arms of the implantation tool is sized and shaped to be a complementary fit within a channel formed between adjacent implant arms on the first end of the implant.

11. The method of claim 10, wherein each of the tool arms of the implantation tool has a base at a proximal end of the tool that tapers in a distal direction to a tip narrower than the base.

12. The method of claim 8, wherein each of the tool arms includes a first surface extending from the tool body along a plane parallel to a longitudinal axis defined by the tool body, each of the tool arms further including a second surface distal to the first surface and extending along a plane parallel to the longitudinal axis, the first and the second surfaces spanning the full width of each of the respective tool arms.

13. A method for implanting an orthopedic implant, comprising: inserting an orthopedic tool having tool arms sized and shaped to complementarily fit into a first end of the implant, the first end including three circumferentially spaced bendable implant arms extending from a central segment and defining a channel between adjacent ones of the implant arms, wherein a surface of each of the tool arms contacts first and second surfaces of corresponding ones of the implant arms and each of the tool arms contacts at least two of the implant arms, wherein the first and the second surfaces of each of the implant arms define planes extending in transverse directions to each other; and
- rotating the tool arms to thread a second end of the implant extending from the central segment and opposing the first end into a bone.

14. The method of claim 13, wherein the first surface of each of the tool arms defines a plane parallel to a longitudinal axis of the tool arm and the second surface of each of the tool arms defines a plane transverse to the respective first surface.

15. The method of claim 13, wherein the bone is a middle phalanx, further comprising the steps of:
- reaming a proximal phalanx;
- inserting a K-wire into the center of the middle phalanx; and
- advancing a tap over the K-wire to prepare the middle phalanx to receive the implant.

16. The method of claim 13, further comprising implanting the first end of the implant into a proximal phalanx after the second end has been threaded into a middle phalanx.

17. The method of claim 16, wherein the second end of the implant includes an outer surface having a helical threading.

18. The method of claim 13, wherein the tool is rotated until a marking disposed on the implant between the first and second ends of the implant meets with a surface of the bone.

19. The method of claim 13, wherein each of the implant arms forms an anchored barb at the first end of the implant.

20. The method of claim 13, further comprising the step of inserting the tool into the first end of the implant and rotating the tool to remove at least a portion of the implant from the bone.

* * * * *